United States Patent
Taniguchi et al.

(10) Patent No.: US 10,816,417 B2
(45) Date of Patent: Oct. 27, 2020

(54) FORCE DETECTOR

(71) Applicants: OMRON HEALTHCARE CO., LTD., Muko-shi, Kyoto (JP); OMRON Corporation, Kyoto-shi, Kyoto (JP); The Ritsumeikan Trust, Kyoto-shi, Kyoto (JP)

(72) Inventors: Minoru Taniguchi, Kyoto (JP); Chisato Tawara, Kyoto (JP); Masao Shimizu, Kyoto (JP); Tsuyoshi Hamaguchi, Kyoto (JP); Sadao Kawamura, Shiga (JP); Hye Jong Kim, Shiga (JP); Yuki Sugano, Shiga (JP)

(73) Assignees: OMRON HEALTHCARE CO., LTD., Kyoto (JP); OMRON CORPORATION, Kyoto (JP); THE RITSUMEIKAN TRUST, Kyoto (JP)

( * ) Notice: Subject to any disclaimer, the term of this patent is extended or adjusted under 35 U.S.C. 154(b) by 81 days.

(21) Appl. No.: 16/291,011

(22) Filed: Mar. 4, 2019

(65) Prior Publication Data

US 2019/0195704 A1 Jun. 27, 2019

Related U.S. Application Data

(63) Continuation of application No. PCT/JP2017/028622, filed on Aug. 7, 2017.

(30) Foreign Application Priority Data

Sep. 5, 2016 (JP) ................................ 2016-172605
Feb. 22, 2017 (JP) ................................ 2017-031275

(51) Int. Cl.
*G01L 1/20* (2006.01)
*G01L 7/06* (2006.01)
(Continued)

(52) U.S. Cl.
CPC ............. *G01L 1/205* (2013.01); *B25J 13/081* (2013.01); *G01L 7/061* (2013.01);
(Continued)

(58) Field of Classification Search
CPC ... G01L 1/20; G01L 7/06; G01L 27/00; G01L 9/12
See application file for complete search history.

(56) References Cited

U.S. PATENT DOCUMENTS 3,750,907 A * 8/1973 Steele ..................... B32B 15/08
                                                                  222/107
5,373,747 A    12/1994 Ogawa et al.
(Continued)

FOREIGN PATENT DOCUMENTS

| CN | 103616117 A | 3/2014 |
| CN | 102483365 B | 3/2015 |

(Continued)

OTHER PUBLICATIONS

Official Communication issued in International Patent Application No. PCT/JP2017/028622, dated Aug. 29, 2017.
(Continued)

*Primary Examiner* — Jewel V Dowtin
(74) *Attorney, Agent, or Firm* — Keating and Bennett, LLP

(57) ABSTRACT

A force detector includes a support, fluid bags, a contact portion, a detector, and a computer. The contact portion is opposite to a side on which the fluid bags are in contact with the support and is adjacent to the fluid bags. The computer obtains information regarding the internal pressures of the fluid bags from the detector. Upon application of an external force to the contact portion from an object, the computer calculates a force acting in a tangential direction on a contact
(Continued)

surface between the object and the contact portion based on a difference between the internal pressures of the fluid bags.

14 Claims, 18 Drawing Sheets

(51) Int. Cl.
    *G01L 27/00*     (2006.01)
    *G01L 9/12*     (2006.01)
    *B25J 13/08*     (2006.01)
    *B25J 15/00*     (2006.01)

(52) U.S. Cl.
    CPC ............. *A61B 2562/0247* (2013.01); *A61B 2562/0252* (2013.01); *A61B 2562/168* (2013.01); *B25J 15/0009* (2013.01)

(56) References Cited

U.S. PATENT DOCUMENTS

| | | | | |
|---|---|---|---|---|
| 5,516,004 | A * | 5/1996 | Lane | B65D 83/625 222/1 |
| 6,134,970 | A | 10/2000 | Kumakawa et al. | |
| 7,124,908 | B2 * | 10/2006 | Sanders | F17C 1/00 220/581 |
| 7,823,457 | B2 * | 11/2010 | Viebach | A61B 1/012 73/718 |
| 8,858,502 | B2 * | 10/2014 | Baxter | G01L 9/12 604/153 |
| 9,903,779 | B2 * | 2/2018 | Hammerschmidt | G01L 27/005 |
| 2012/0210799 | A1 * | 8/2012 | Motoyama | G01L 19/145 73/716 |
| 2015/0127159 | A1 | 5/2015 | Kamiya et al. | |
| 2017/0233245 | A1 * | 8/2017 | Duqi | G01L 9/0054 257/419 |

FOREIGN PATENT DOCUMENTS

| | | |
|---|---|---|
| CN | 104614118 A | 5/2015 |
| JP | 48-26553 B1 | 8/1973 |
| JP | 4-304988 A | 10/1992 |
| JP | 06-341912 A | 12/1994 |
| JP | 2000-111420 A | 4/2000 |
| JP | 3183465 B2 | 7/2001 |
| JP | 2011-047710 A | 3/2011 |
| JP | 4777453 B2 | 9/2011 |
| JP | 5107979 B2 | 12/2012 |

OTHER PUBLICATIONS

Official Communication issued in corresponding Japanese Patent Application No. 2017-031275, dated Jan. 7, 2020.
Official Communication issued in corresponding Chinese Patent Application No. 201780054172.9 dated May 6, 2020.
Hao et al., "Analysis of Deformation and Pressure of Porous Circular Cylinder in Potential Flow", Chinese Quarterly of Mechanics, vol. 37 No. 1, Mar. 2016, pp. 176-183.

* cited by examiner

FIG.30
| OUTER SHAPE | RECTANGLE | EQUILATERAL TRIANGLE | SQUARE | REGULAR PENTAGON |
|---|---|---|---|---|
| $V[cm^3]$ | 27.8 | 28.0 | 27.8 | 29.0 |
| $T[mm]$ | 15.9 | 25.5 | 26.7 | 28.2 |
| $H[mm]$ | 24, 150 | 66 | 50 | 59 |
| $L[mm]$ | 150, 24 | 76 | 50 | 38 |
| $L/H$ | 0.16, 6.25 | 0.87 | 1.00 | 1.54 |
V : VOLUME DURING PRESSURIZATION AT 20 kPa
H : LENGTH OF EACH SIDE TO OPPOSITE SIDE/
    OPPOSITE ANGLE DURING NON-PRESSURIZATION
T : THICKNESS DURING PRESSURIZATION AT 20 kPa
L : LENGTH OF EACH SIDE DURING NON-PRESSURIZATION
FIG.31
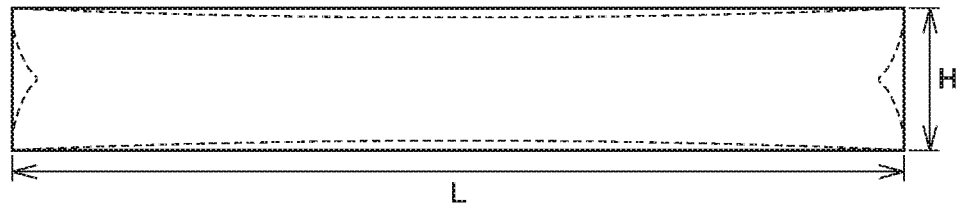
FIG.32
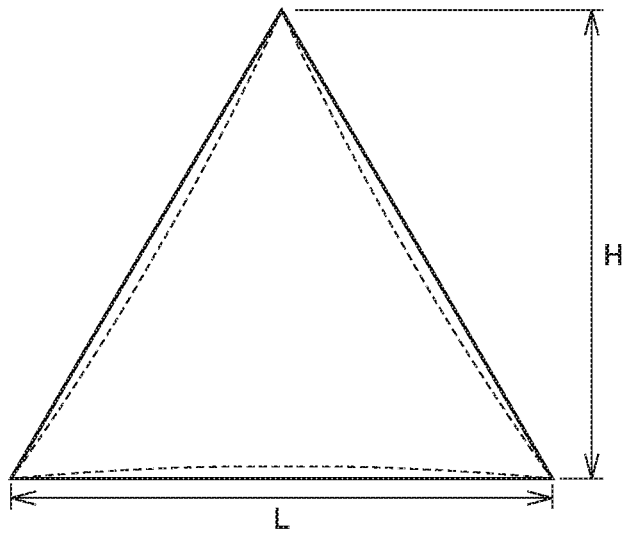

FORCE DETECTOR

CROSS REFERENCE TO RELATED APPLICATIONS

This application claims the benefit of priority to Japanese Patent Application No. 2016-172605 filed on Sep. 5, 2016 and Japanese Patent Application No. 2017-031275 filed on Feb. 22, 2017, and is a Continuation Application of PCT Application No. PCT/JP2017/028622 filed on Aug. 7, 2017. The entire contents of each application are hereby incorporated herein by reference.

BACKGROUND OF THE INVENTION

1. Field of the Invention

The present invention relates to force detectors.

2. Description of the Background Art

Japanese Patent Laying-Open No. 04-304988 discloses the invention related to robot hands and describes silicon rubber as an example material for a member (elastic cap) forming fingertips of the robot hand. Along with this, robot hands with an inflatable structure have been under development in recent years. A plastic sheet is used to form a fluid bag, and this fluid bag is filled with a fluid such as air.

The inflatable robot uses such a fluid bag as a structural member or an actuator. The inflatable robot including the fluid bag can be driven by air pressure and can exhibit characteristics of being lightweight and flexible compared with a conventional robot formed of metal material, and is accordingly expected to be used in the health equipment field, nursing care equipment field, and any other field.

In the fields of health equipment and nurse care equipment, a robot and a human mechanically interact with each other frequently, leading to demands for appropriately controlling a force imparted to the human by the inflatable robot. For example, when the inflatable robot obtains physical data or massages a human body, an appropriate mechanical contact between the robot and the human body is required.

Common industrial robots have used force sensors (force detectors) such as load cells or torque sensors for force control. These force sensors are formed of a rigid body and have a certain mass. These force sensors, if used in inflatable robots, may fail to exhibit the characteristics of being lightweight and flexible which are inherent in the inflator structure.

The robot hand disclosed in Japanese Patent Laying-Open No. 04-304988 has fingertips each having an elastic cap with a hollow portion, and is configured to detect the internal pressure of the hollow portion to determine a contact force generated between the fingertip and an object. This technique can calculate, of the contact force generated between the fingertip and the object, a force acting in a normal direction on a contact surface between the object and the fingertip, but fails to calculate a force acting on the contact surface in a tangential direction.

SUMMARY OF THE INVENTION

Example embodiments of the present invention provide force detectors each capable of calculating a force acting on a contact surface in a tangential direction.

A force detector according to a first aspect of the present invention includes a support, a first fluid container, a second fluid container, a contact portion, a detector, and a computer. The first fluid container and the second fluid container are supported by the support, have a bag shape defined by a sheet-shaped member, and are adjacent to each other. The contact portion is disposed opposite to a side on which the first fluid container and the second fluid container are in contact with the support and is adjacent to both the first fluid container and the second fluid container. The detector is configured to detect an internal pressure of the first fluid container and an internal pressure of the second fluid container. The computer is configured or programmed to obtain information regarding the internal pressure of the first fluid container and the internal pressure of the second fluid container from the detector and, upon application of an external force to the contact portion from an object, calculate a force acting in a tangential direction on a contact surface between the object and the contact portion. Upon application of the external force to the contact portion from the object, the external force applied to the contact portion from the object is imparted to both the first fluid container and the second fluid container through the contact portion. Upon application of the external force to the contact portion from the object, the computer calculates the force acting on the contact surface in the tangential direction based on a difference between the internal pressure of the first fluid container and the internal pressure of the second fluid container.

A force detector according to a second aspect of the present invention includes a support, a first fluid container, a second fluid container, a third fluid container, a fourth fluid container, a contact portion, a detector, and a computer. The first fluid container, the second fluid container, the third fluid container, and the fourth fluid container are supported by the support, have a bag shape defined by a sheet-shaped member, and are adjacent to each other. The contact portion is disposed opposite to a side on which the first fluid container, the second fluid container, the third fluid container, and the fourth fluid container are in contact with the support and is provided to be adjacent to all the first fluid container, the second fluid container, the third fluid container, and the fourth fluid container. The detector is configured to detect an internal pressure of the first fluid container, an internal pressure of the second fluid container, an internal pressure of the third fluid container, and an internal pressure of the fourth fluid container. The computer is configured or programmed to obtain information regarding the internal pressure of the first fluid container, the internal pressure of the second fluid container, the internal pressure of the third fluid container, and the internal pressure of the fourth fluid container from the detector and, upon application of an external force to the contact portion from an object, calculate a force acting in a tangential direction on a contact surface between the object and the contact portion. Upon application of the external force to the contact portion from the object, the external force applied to the contact portion from the object is imparted to all the first fluid container, the second fluid container, the third fluid container, and the fourth fluid container through the contact portion. When a sum of internal pressures of two fluid containers of the first fluid container, the second fluid container, the third fluid container, and the fourth fluid container is defined as a first internal pressure and a sum of internal pressures of the other two fluid containers of the first fluid container, the second fluid container, the third fluid container, and the fourth fluid container is defined as a second internal pressure, upon application of the external force to the contact portion from the object, the computer calculates the force acting on the contact surface in the tangential direction based on a difference between the first internal pressure and the second internal pressure.

The above and other elements, features, steps, characteristics and advantages of the present invention will become more apparent from the following detailed description of example embodiments with reference to the attached drawings.

BRIEF DESCRIPTION OF THE DRAWINGS

FIG. 30 shows experimental conditions of Verification Experiment 6 of an example embodiment of the present invention.

FIG. 31 is a plan view of a rectangular fluid bag used in Verification Experiment 6 of an example embodiment of the present invention.

FIG. 32 is a plan view of a fluid bag having an equilateral triangle shape used in Verification Experiment 6 of an example embodiment of the present invention.

DETAILED DESCRIPTION OF EXAMPLE EMBODIMENTS

Figure 1:
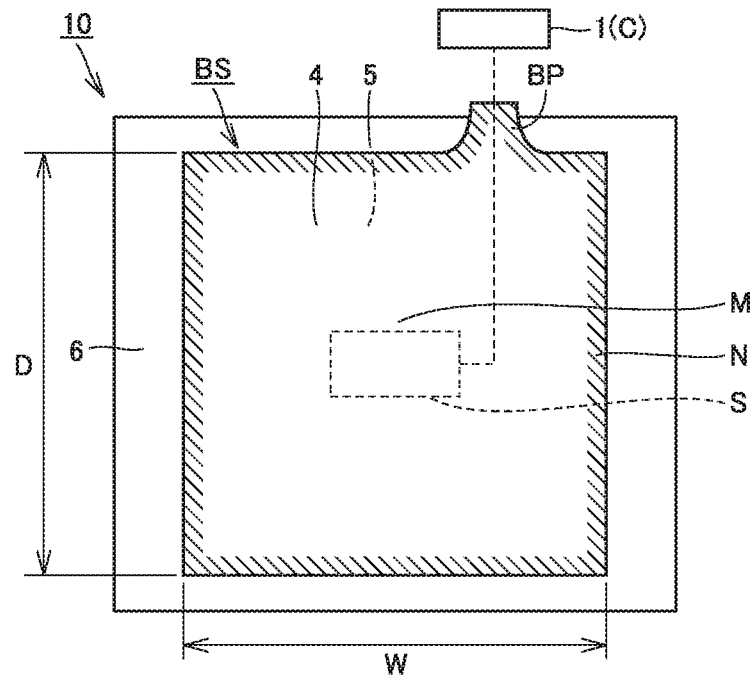
FIG. 1 is a plan view of a force detector 10 in a reference art.
Figure 2:
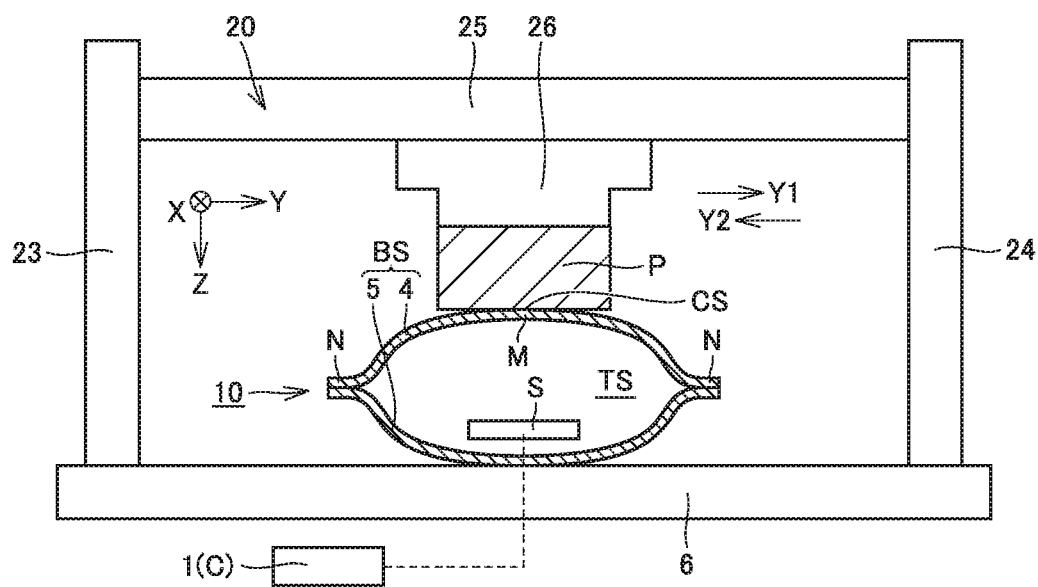
FIG. 2 is a sectional view of force detector 10 and the like in the reference art.
Figure 3:
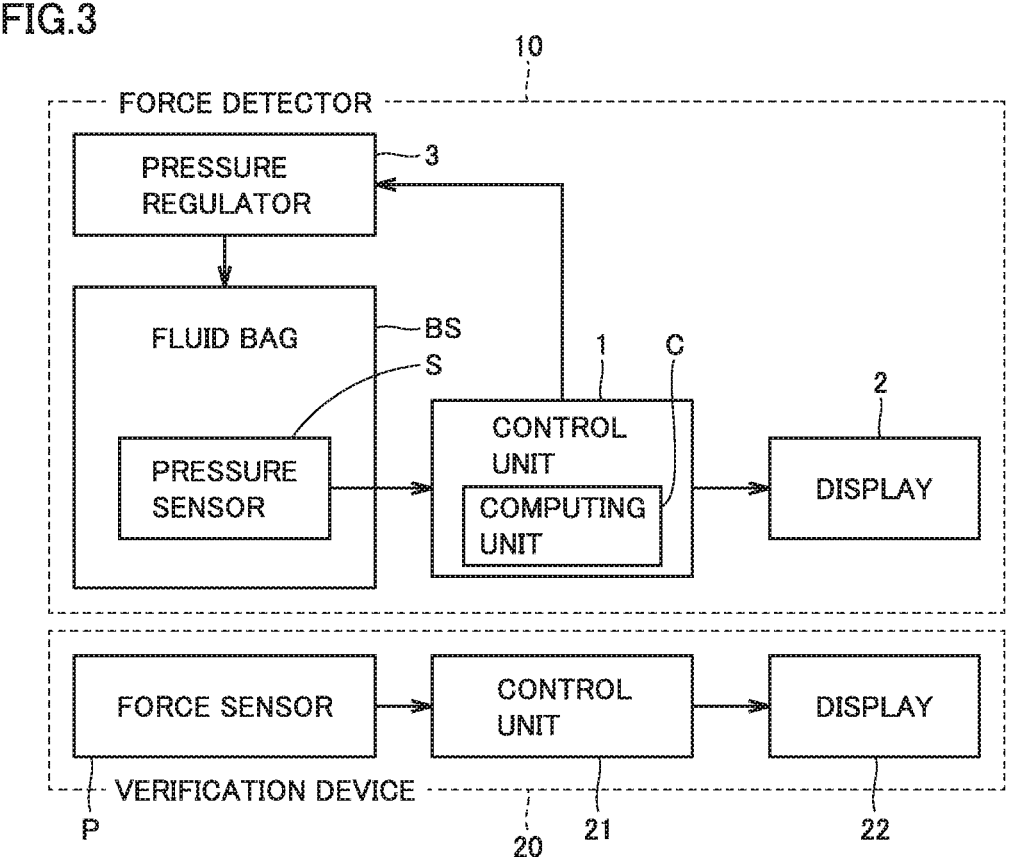
FIG. 3 is a block diagram showing a functional configuration of force detector 10 and the like in the reference art.

Prior to the description of example embodiments of the present invention, a force detector 10 in a reference art will be described with reference to FIGS. 1 to 6. FIG. 1 is a plan view of force detector 10, FIG. 2 is a sectional view of force detector 10 and the like, and FIG. 3 is a block diagram showing a functional configuration of force detector 10 and the like. FIGS. 2 and 3 also show a verification device 20 for verifying the performance of force detector 10, in addition to force detector 10.

As shown in FIGS. 1 to 3, a force detector 10 includes a control unit 1, a display 2 (FIG. 3), a pressure regulator 3 (FIG. 3), a fluid bag BS, a support 6 (FIGS. 1 and 2), and a pressure sensor S. Control unit 1 includes a computer C and, for example, receives an externally input signal to control the operation of pressure regulator 3 and cause display 2 to display a value calculated by computer C. Control unit 1 and display 2 may be configured by, for example, a microcomputer or PC.

Fluid bag BS is defined by sheet-shaped members 4 and 5 (FIGS. 1 and 2) bonded to each other. Sheet-shaped members 4 and 5 have the same shape. In one example, a width W is 100 mm, a length D is 100 mm, and a material for the sheet-shaped members is plastic such as polyethylene.

Each of sheet-shaped members 4 and 5 has a main front surface portion M and an outer peripheral portion N located on the outer periphery of main front surface portion M. Fluid bag BS has a bag shape defined by outer peripheral portions N of sheet-shaped members 4 and 5 which are bonded to each other. A sealed space TS is defined inside fluid bag BS, and space TS is filled with a fluid (typically, gas such as air) by pressure regulator 3.

Pressure sensor S is housed in fluid bag BS. Pressure sensor S detects the internal pressure of fluid bag BS (space TS). Pressure sensor S may be an absolute pressure sensor "2SMPB-01 (pressure measuring range: 30 kPa to 110 kPa)" available from OMRON Corporation. A port BP is provided in a portion of the periphery of fluid bag BS, and pressure sensor S and control unit 1 are connectable to each other through port BP.

Space TS in fluid bag BS and pressure regulator 3 are configured to be connectable to each other through port BP. Pressure sensor S shown in FIGS. 1 and 2 is disposed inside fluid bag BS and is configured independently of pressure regulator 3. Pressure sensor S can be disposed outside fluid bag BS as long as it can detect the internal pressure of fluid bag BS (space TS) and can be incorporated into pressure regulator 3 as part of the function of pressure regulator 3.

Fluid bag BS is disposed on support 6 such that sheet-shaped member 5 is in contact with support 6. Support 6 is, for example, a structural member defining the frame of an inflatable robot. In order to prevent fluid bag BS (sheet-shaped member 5) from sliding on the surface of support 6 when fluid bag BS (sheet-shaped member 4) receives an external force, a silicon sheet, an adhesive, or the like may be provided between fluid bag BS (sheet-shaped member 5) and support 6.

A configuration can be made without a silicon sheet, an adhesive, or the like provided between fluid bag BS (sheet-shaped member 5) and support 6 if the frictional force between fluid bag BS (sheet-shaped member 5) and support 6 is sufficiently large or if the position of fluid bag BS is fixed by any fixing means to prevent fluid bag BS (sheet-shaped member 5) from sliding on the surface of support 6 even when fluid bag BS (sheet-shaped member 4) receives an external force.

Verification Experiment 1

An experiment for verifying the performance of force detector 10 configured as described above will now be described. Verification device 20 (FIGS. 2 and 3) used in the experiment includes a control unit 21, a display 22, support rods 23 and 24, a rail 25, a slider 26, and a force sensor P.

Support rods 23 and 24 are fixed on support 6. Rail 25 is suspended between support rods 23 and 24 and is configured to be movable in a direction (Z-axis positive direction) in which rail 25 approaches fluid bag BS on support 6 and a direction (Z-axis negative direction) in which rail 25 leaves fluid bag BS. Slider 26 is provided on rail 25 (the lower portion of rail 25) and is configured to be movable in a Y-axis direction (Y1 direction and Y2 direction) orthogonal to the Z-axis direction.

Force sensor P has an approximately cylindrical shape and is secured to the lower surface of slider 26. Force sensor P may be a capacitive six-axis force sensor "WDF-6M200-3: rated loads of 200 N (Fx, Fy, Fz) and 3 Nm (Mx, My, Mz)" available from WACHO-TECH Inc. Force sensor P is movable relative to fluid bag BS on support 6 by rail 25 moving in the Z-axis direction or slider 26 moving in the Y-axis direction.

Verification device 20 regards force sensor P as an external object (that imparts force to force detector 10). A contact surface CS (FIG. 2) is formed between force sensor P and sheet-shaped member 4 of fluid bag BS. The Z-axis direction corresponds to the direction normal to contact surface CS between force sensor P and fluid bag BS, and the Y-axis direction corresponds to the direction tangential to contact surface CS.

Moving rail 25 and slider 26 applies the forces in a normal direction and a tangential direction to fluid bag BS. At this time, the internal pressure of fluid bag BS is detected with pressure sensor S in fluid bag BS, and the contact force (including the force in the normal direction and the force in the tangential direction) acting on contact surface CS is detected with force sensor P.

Specifically, (1) an initial pressure is imparted to fluid bag BS, and wait for 5 [s] from its beginning, (2) next, force sensor P is moved in the Z-axis positive direction by movement of rail 25 to apply a force to fluid bag BS, and (3) in the state of (2) above, force sensor P is moved in the Y-axis positive direction by movement of slider 26 to apply a force (a force in the tangential direction) to fluid bag BS.

Figure 4:
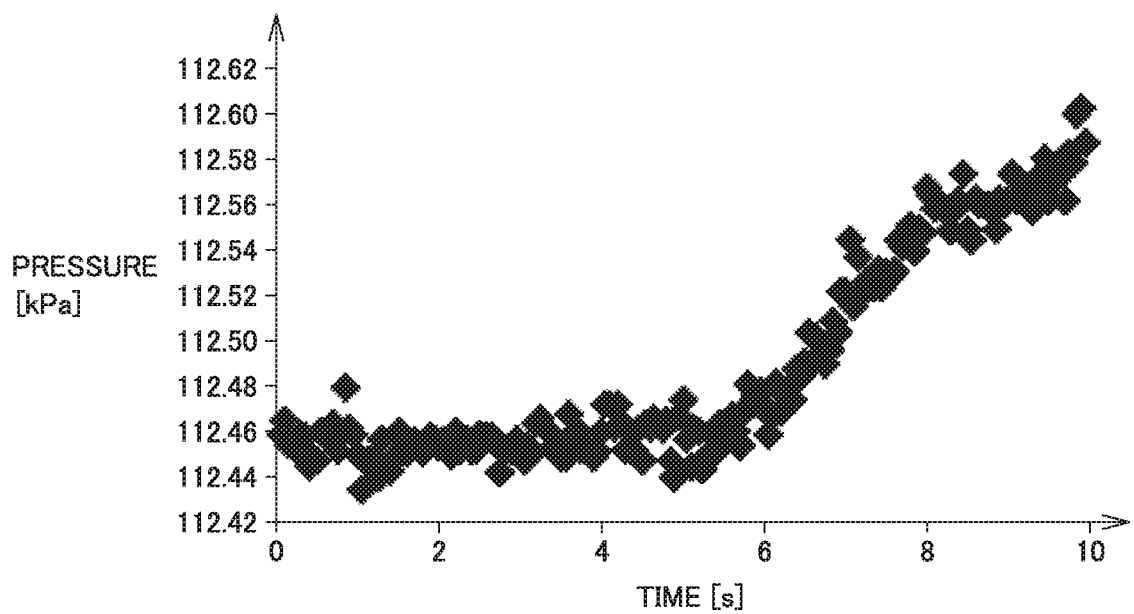
FIG. 4 is a graph showing a change in the internal pressure of a fluid bag BS for Verification Experiment 1 in the reference art.
Figure 5:
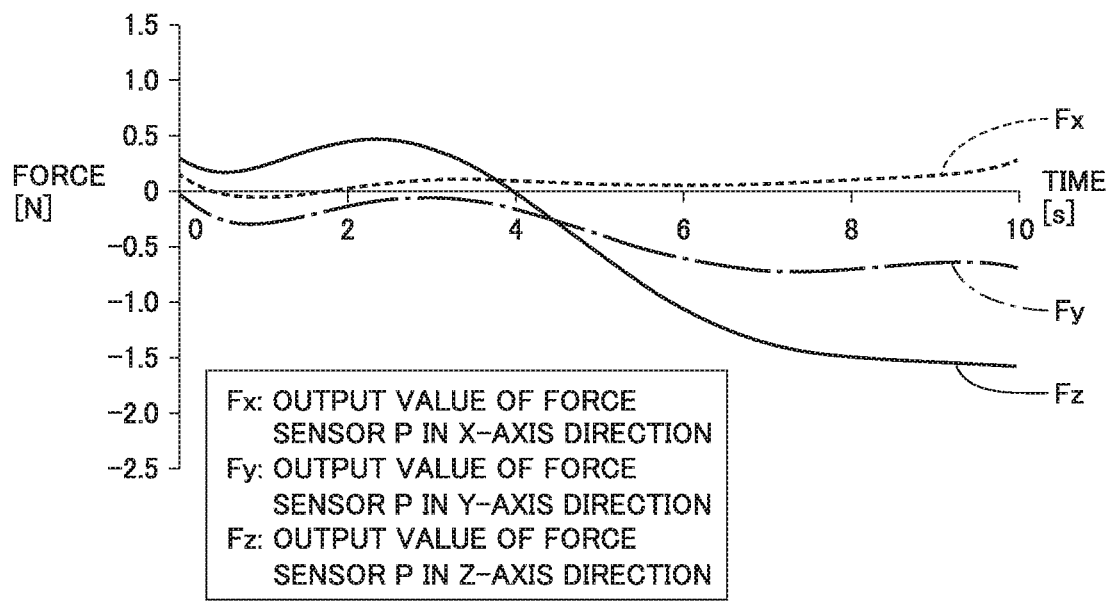
FIG. 5 is a graph showing changes in contact forces Fx, Fy, and Fz (all of which are polynomials) acting on a contact surface CS for Verification Experiment 1 in the reference art.

FIG. 4 shows output values obtained from pressure sensor S in fluid bag BS during the above operations of (1) to (3), showing changes in the internal pressure of fluid bag BS. FIG. 5 shows output values obtained from force sensor P during the above operations of (1) to (3), showing changes in contact forces Fx, Fy, and Fz (all of which are polynomials) acting on contact surface CS. The data shown in FIG. 4 and the data shown in FIG. 5 are actually the results obtained when the operations of (2) and (3) are performed manually (when force sensor P and fluid bag BS are moved relative to each other).

It is found as shown in FIGS. 4 and 5 that the output values of force sensor P in the Z-axis direction and the Y-axis direction change from about 5 [s] at which the application of the force in the Z-axis positive direction to fluid bag BS is started (see FIG. 5). Along with this (see FIG. 4), the output value of pressure sensor S also changes. It is thus conceivable that force Fy in the tangential direction and force Fz in the normal direction may have deformed fluid bag BS with pressure sensor S provided therein, and the deformation of fluid bag BS may have changed the internal pressure of fluid bag BS. It is accordingly conceivable from the results shown in FIGS. 4 and 5 that force detector 10 includes only one pressure sensor S, and accordingly, substantially cannot calculate or estimate both the forces in two directions (force Fy in the tangential direction and force Fz in the normal direction).

Verification Experiment 2

Figure 6:
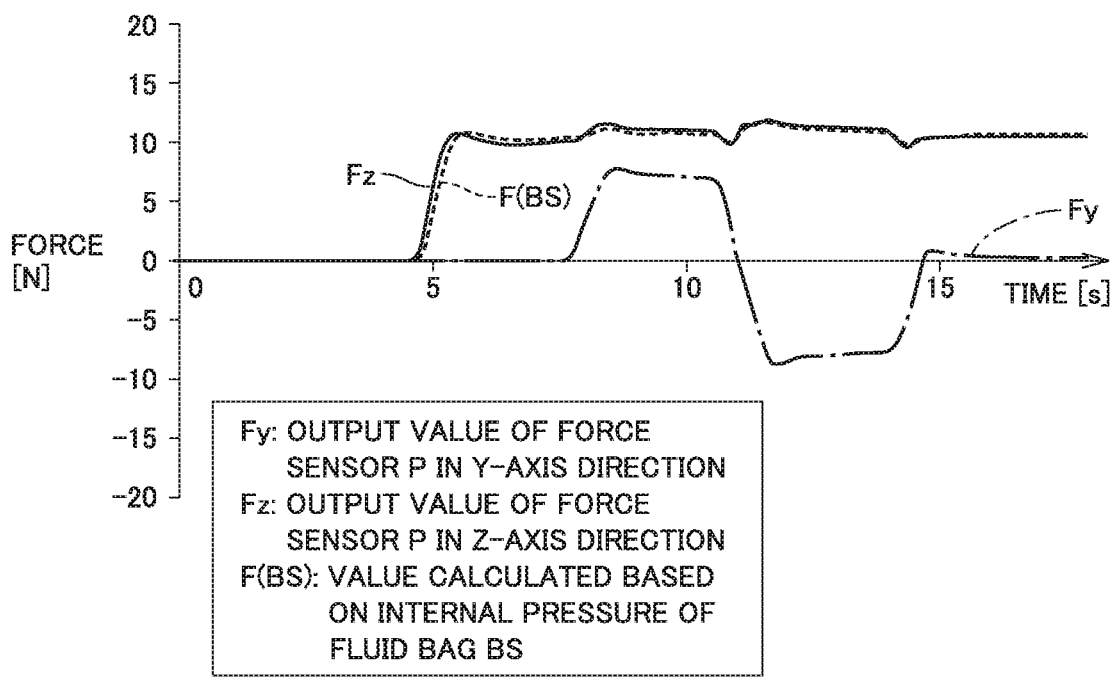
FIG. 6 is a graph for Verification Experiment 2 in the reference art.

With reference to FIG. 6, another verification experiment was performed using a device similar to each device shown in FIGS. 2 and 3. Herein, the relationship among an external force F, an internal pressure P, and an initial pressure Ps is given in fluid bag BS (100 mm×100 mm) having an inflatable structure as represented by an expression (A) below.

$$F=\alpha(Ps)P+\beta(Ps) \quad (A)$$

In the above expression (A), $\alpha$ and $\beta$ are functions determined by initial pressure Ps in fluid bag BS.

A gage pressure sensor "2SMPP-02" available from OMRON Corporation was used as pressure sensor S. This sensor was connected to fluid bag BS of 100 mm×100 mm through a tube. The value of the output voltage due to a change in the internal pressure of fluid bag BS was obtained as voltage data using an amplifier circuit or an A/D converter.

A six-axis force sensor "PFS080YA" available from Leptrino Co. Ltd was used as force sensor P for measuring external force. Herein, a silicon rubber sheet was disposed between fluid bag BS and force sensor P and between fluid bag BS and support 6 to reduce or prevent a slide therebetween.

As shown in FIG. 6, force sensor P was moved from 5 [s] in the Z-axis positive direction relative to fluid bag BS applied with an initial pressure and the position thereof is fixed, thereby imparting a certain force to fluid bag BS in the normal direction. In this state, force sensor P was moved horizontally in the Y-axis direction from 10 [s], thereby imparting a force in the tangential direction. The force in the tangential direction imparted in this experiment is 9.8 N, and a displacement in the Y-axis direction is ±10 mm.

As shown in FIG. 6, for the Z-axis direction, a value of the above expression (A), that is, a value (equivalent) calculated based on the internal pressure of the fluid bag (F (BS)) shows a waveform close to that of an output value of force sensor p in the Z-axis direction. In contrast, it is found that for the Y-axis direction, a value (equivalent) calculated based on the internal pressure of the fluid bag (F (BS)) is not relevant to the output value of force sensor P in the Y-axis direction, and accordingly, the measurement of the force in the tangential direction failed. It is thus conceivable also from the results shown in FIG. 6 that force detector 10 includes only one pressure sensor S, and accordingly, substantially cannot calculate or estimate both the forces in two directions (force Fy in the tangential direction and force Fz in the normal direction).

Example embodiments of the present invention will now be described with reference to the drawings. The same or corresponding parts are denoted by the same reference numerals, and repetitive description may be omitted.

Example Embodiment 1

Figure 7:
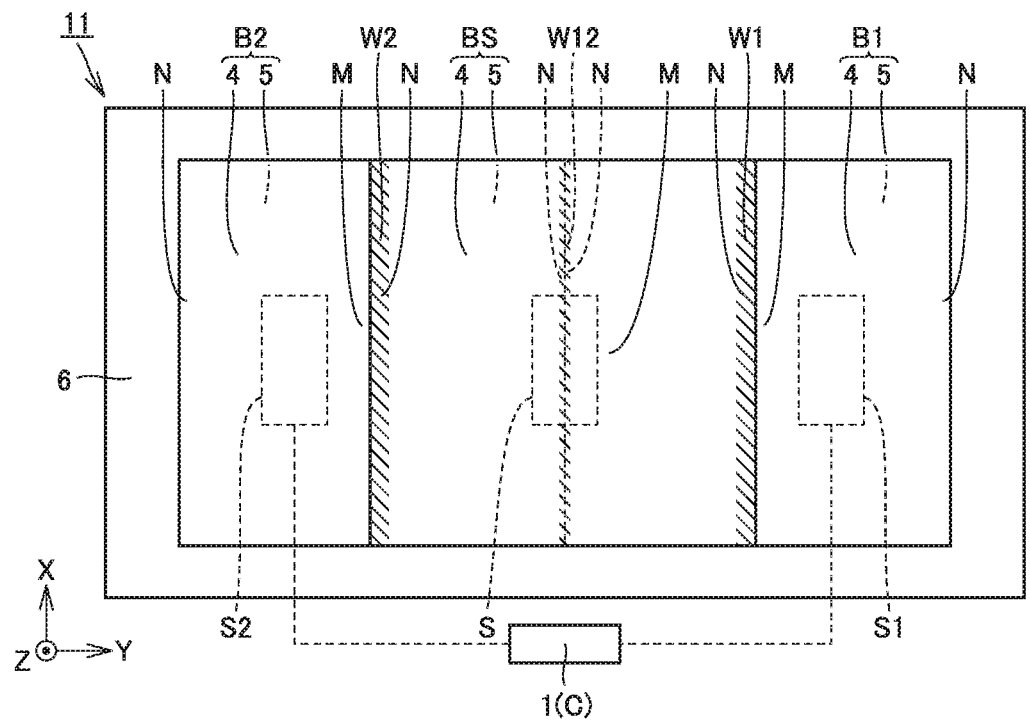
FIG. 7 is a plan view of a force detector 11 in Example Embodiment 1 of the present invention.
Figure 8:
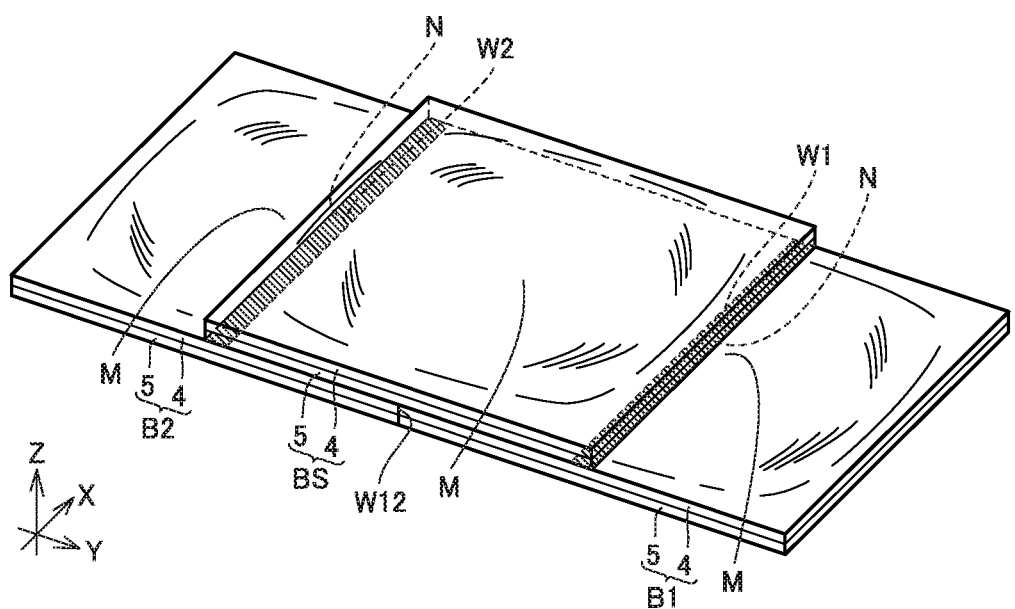
FIG. 8 is a perspective view of fluid bags BS, B1, and B2 of force detector 11 in Example Embodiment 1 of the present invention.
Figure 9:
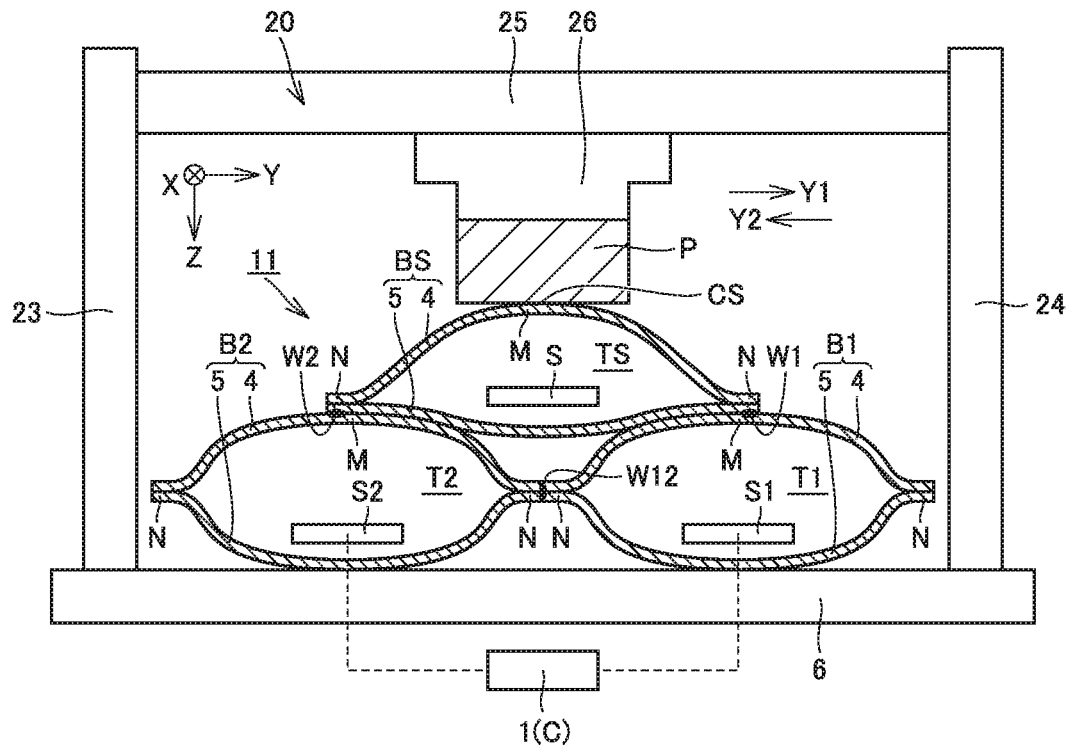
FIG. 9 is a sectional view of force detector 11 and the like in Example Embodiment 1 of the present invention.

A force detector 11 in Example Embodiment 1 will be described with reference to FIGS. 7 to 9. FIG. 7 is a plan view of force detector 11, FIG. 8 is a perspective view of fluid bags BS, B1, and B2 of force detector 11, and FIG. 9 is a sectional view of force detector 11 and the like. FIG. 9 also shows a verification device 20 to verify the performance of force detector 11, in addition to force detector 11.

As shown in FIGS. 7 to 9, force detector 11 includes a controller 1, fluid bags BS, B1, and B2, a support 6 (FIGS. 7 and 9), and pressure sensors S1 and S2. Although a detailed configuration will be described below, fluid bag BS corresponds to a "contact portion", fluid bag B1 corresponds to a "first fluid container", and fluid bag B2 corresponds to a "second fluid container". Pressure sensors S1 and S2 correspond to a "detector configured to detect an internal pressure of the first fluid container and an internal pressure of the second fluid container".

Controller 1 (FIGS. 7 and 9) includes a computer C and, for example, receives an externally input signal to control the operation of a pressure regulator (not shown) and cause a display (not shown) to display a value calculated by computer C. Controller 1 and the display (not shown) can be configured by a microcomputer or PC, for example.

Fluid bags BS, B1, and B2 have a configuration similar to that of fluid bag BS in the reference art described above. Each of fluid bags BS, B1, and B2 is defined by sheet-shaped members 4 and 5 bonded to each other. Sheet-shaped members 4 and 5 have the same size and shape, 100 mm×100 mm, and the material therefor is plastic such as polyethylene.

Each of sheet-shaped members 4 and 5 has a main front surface portion M and an outer peripheral portion N located on the outer periphery of main front surface portion M. Each of fluid bags BS, B1, and B2 has a bag shape defined by outer peripheral portions N of sheet-shaped members 4 and 5 which are bonded to each other. Sealed spaces TS, T1, and T2 (FIG. 9) are provided inside fluid bags BS, B1, and B2, respectively, and spaces TS, T1, and T2 are filled with a fluid (typically, gas such as air) by the pressure regulator.

Fluid bags B1 and B2 are adjacent to each other in the Y-axis direction. Fluid bags B1 and B2 are disposed on support 6 such that sheet-shaped member 5 of each of fluid bags B1 and B2 is in contact with support 6. Support 6 is, for example, a structural member defining a frame of an inflatable robot. It suffices that a silicon sheet, an adhesive, or the like is provided between fluid bags B1 and B2 (sheet-shaped members 5) and support 6 in order to prevent fluid bags B1 and B2 (sheet-shaped members 5) from sliding on the surface of support 6 when fluid bags B1 and B2 (sheet-shaped members 4) receive an external force.

A configuration may be made without a silicon sheet, an adhesive, or the like provided between fluid bags B1 and B2 (sheet-shaped member 5) and support 6 if a frictional force between fluid bags B1 and B2 (sheet-shaped member 5) and support 6 is sufficiently large or if the positions of fluid bags B1 and B2 are fixed by any fixing structure or material to prevent fluid bags B1 and B2 (sheet-shaped member 5) from sliding on the surface of support 6 even when fluid bags B1 and B2 (sheet-shaped member 4) receive an external force.

Outer peripheral portion N of fluid bag B1 which is located in the Y-axis negative direction (on the negative side in the Y-axis direction) and outer peripheral portion N of fluid bag B2 which is located in the Y-axis positive direction (on the positive side in the Y-axis direction) are bonded to each other using a bonding method or material such as welding or an adhesive. A bonding portion W12 extending linearly is located between outer peripheral portions N.

Bonding portion W12 shown in FIGS. 8 and 9 is located between the ends of sheet-shaped members 4 and 5 in the Y-axis direction. In actuality, bonding portion W12 can be easily defined by portions of outer peripheral portions N of fluid bags B1 and B2, which are layered in Z-axis direction and then bonded to each other.

As described above, fluid bag B1 corresponds to the "first fluid container", and fluid bag B2 corresponds to the "second fluid container". The first fluid container and the second fluid container in the present example embodiment are respectively defined by two fluid bags B1 and B2 independent of each other. Fluid bags B1 and B2 are bonded to each other and are adjacent to each other in the Y-axis direction. The first fluid container and the second fluid container can be adjacent to each other (see FIG. 19) by partitioning the internal space of one fluid bag or one or more fluid bags, which will be described below with reference to FIG. 19.

Fluid bag BS is disposed opposite to the side on which fluid bags B1 and B2 are in contact with support 6 (i.e., opposite to the side on which support 6 is located as viewed from fluid bags B1 and B2) and is provided to be adjacent to both of fluid bags B1 and B2. Fluid bag BS is disposed on fluid bags B1 and B2 such that sheet-shaped member 5 of fluid bag BS is in contact with sheet-shaped members 4 of fluid bags B1 and B2. As described above, fluid bag BS corresponds to the "contact portion".

Part of outer peripheral portion N of fluid bag BS defining the contact portion, specifically, part of outer peripheral portion N which is located in the Y-axis positive direction (on the positive side in the Y-axis direction), and part of main front surface portion M of sheet-shaped member 4 defining fluid bag B1 are bonded to each other using a bonding method or material welding or an adhesive. A bonding portion W1 extending linearly is provided therebetween.

Part of outer peripheral portion N of fluid bag BS defining the contact portion, specifically, part of outer peripheral portion N which is located in the Y-axis negative direction (on the negative side in the Y-axis direction), and part of main front surface portion M of sheet-shaped member 4 defining fluid bag B2 are bonded to each other using a bonding method or material such as welding or an adhesive. A bonding portion W2 extending linearly is provided therebetween.

In the present example embodiment, fluid bag BS as the contact portion is defined by one fluid bag BS independent of fluid bags B1 and B2. Fluid bag BS is bonded to fluid bags B1 and B2 and is adjacent to fluid bags B1 and B2. The contact portion can also be adjacent to the first and second fluid containers (see FIG. 19) by partitioning the internal space of one fluid bag or one or more fluid bags, which will be described below with reference to FIG. 19.

As described above, fluid bag BS corresponds to the "contact portion". The contact portion in the present example embodiment is defined by fluid bag BS with a fluid contained therein. It is not necessarily required that the contact portion be defined by fluid bag BS, which will be described below with reference to FIGS. 19, 20, and 22. The contact portion may be defined by, for example, a plate-shaped member.

Pressure sensors S1 and S2 are housed in fluid bags B1 and B2, respectively. Pressure sensors S1 and S2 detect the internal pressures of fluid bags B1 and B2 (spaces T1 and T2), respectively. Pressure sensors S1 and S2 each may be an absolute pressure sensor "2SMPB-01 (pressure measuring range: 30 kPa to 110 kPa)" available from OMRON Corporation.

Pressure sensors S1 and S2 are disposed inside fluid bags B1 and B2 and are configured independently of the pressure regulator. Pressure sensors S1 and S2 may be disposed outside fluid bags B1 and B2 as long as they can detect the internal pressures of fluid bags B1 and B2 (spaces T1 and T2), and may be incorporated into the pressure regulator as part of the function of the pressure regulator.

As described above, pressure sensors S1 and S2 correspond to the "detector configured to detect an internal pressure of the first fluid container (herein, fluid bag B1) and an internal pressure of the second fluid container (herein, fluid bag B2)". Although two independent pressure sensors S1 and S2 are used to detect the internal pressures of fluid bags B1 and B2 in the present example embodiment, the "detector" may be defined by one pressure sensor that can detect the internal pressures of fluid bags B1 and B2.

As described above, bonding portion W12 is provided between fluid bags B1 and B2, bonding portion W1 is provided between fluid bags BS and B1, and bonding portion W2 is provided between fluid bags BS and B2, so that fluid bags BS, B1, and B2 are restrained by each other. When an external force is applied to fluid bag BS (contact portion) from an object, the external force applied to fluid bag BS (contact portion) from the object is imparted to fluid bag B1 (first fluid container) and fluid bag B2 (second fluid container) through fluid bag BS (contact portion). When a shear force is generated by application of the force in the Y-axis direction from above fluid bag BS, one of the contact force (shear force) between fluid bags BS and B1 and the contact force (shear force) between fluid bags BS and B2 becomes higher and the other contact force becomes lower, causing a difference in internal pressure between fluid bags B1 and B2.

Computer C included in controller 1 obtains information regarding the internal pressure of fluid bag B1 and the internal pressure of fluid bag B2 from the detector (pressure sensors S1 and S2) and calculates a force acting in the tangential direction on contact surface CS between the object and the contact portion when an external force is applied to the contact portion (fluid bag BS) from the object. A specific calculation method is as described below.

Figure 10:
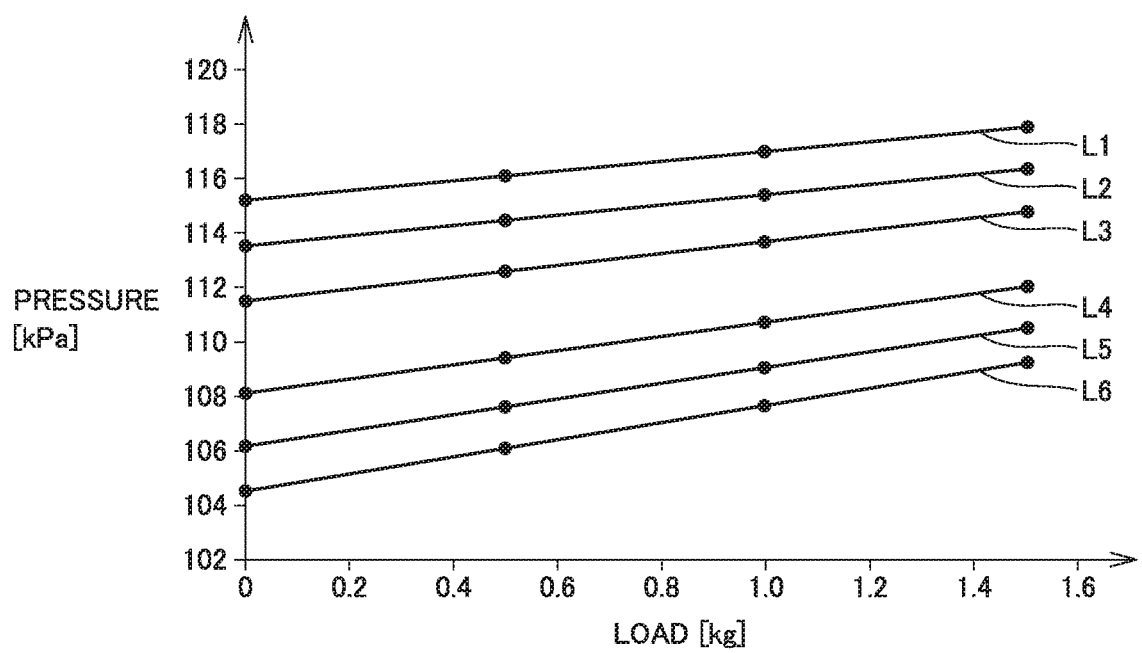
FIG. 10 is a graph for illustrating a function referred to by a computer C in Example Embodiment 1 of the present invention.

With reference to FIG. 10, as described for the above expression (A) [$F=\alpha(Ps)P+\beta(Ps)$], the internal pressure of fluid bag B1 is adjusted to provide an appropriate initial pressure, and the application of a load to fluid bag B1 in the direction in which fluid bag B1 inflates is started, so that the load applied to fluid bag B1 and the internal pressure of fluid bag B1 have a linear relationship. This relationship holds at any appropriate initial pressure (e.g., lines L1 to L6 shown in FIG. 10), and the same applies to fluid bag B2.

In the present example embodiment, the force in the normal direction acting on contact surface CS between fluid bag BS and force sensor P is represented by Fn, and the force acting on contact surface CS in the tangential direction is represented by Ft. Assume that the internal pressures of fluid bags B1 and B2 are P1 and P2, respectively, and the initial pressures of fluid bags B1 and B2 are Ps1 and Ps2, respectively, expressions (B) and (C) below are satisfied.

$$Fn=\{\alpha(Ps1)P1+\beta(Ps1)\}+\{\alpha(Ps2)P2+\beta(Ps2)\} \quad (B)$$

$$Ft=\{\alpha(Ps1)P1+\beta(Ps1)\}-\{\alpha(Ps2)P2+\beta(Ps2)\} \quad (C)$$

In the above expressions (B) and (C), $\alpha$ and $\beta$ are functions determined by initial pressures Ps1 and Ps2 in fluid bags B1 and B2 and can be prepared by, for example, a preparatory experiment.

That is to say, the force acting on contact surface CS in the tangential direction can be calculated based on the sum of the internal pressure of fluid bag B1 and the internal pressure of fluid bag B2. The force acting on contact surface CS in the tangential direction can be calculated based on the difference between the internal pressure of fluid bag B1 and the internal pressure of fluid bag B2.

Computer C of controller 1 included in force detector 11 at least uses the above expression (C) to calculate the force acting on contact surface CS in the tangential direction based on the difference between the internal pressure of fluid bag B1 and the internal pressure of fluid bag B2. In a preferable manner, computer C uses the above expression (B) to calculate the force in the tangential direction, as well as the force acting on contact surface CS in the normal direction based on the sum of the internal pressure of fluid bag B1 and the internal pressure of fluid bag B2.

Verification Experiment 1

An experiment for verifying the performance of force detector 11 configured as described above will now be described. Verification device 20 (FIG. 9) used in the experiment has a configuration similar to that in the reference art described above. Pressure sensor S housed in fluid bag BS is an element of verification device 20 and is not included as an element of force detector 11.

Moving rail 25 and slider 26 applies a force in the normal direction and a force in the tangential direction to fluid bag BS. At this time, pressure sensor S in fluid bag BS is used to detect the internal pressure of fluid bag BS, pressure sensor S1 in fluid bag B1 is used to detect the internal pressure of fluid bag B1, pressure sensor S2 in fluid bag B2 is used to detect the internal pressure of fluid bag B2, and force sensor P is used to detect the contact force (including a force in the normal direction and a force in the tangential direction) acting on contact surface CS.

Specifically, (1) after a lapse of some time from application of an initial pressure to fluid bags BS, B1, and B2, rail 25 holding force sensor P and slider 26 is moved in the Z-axis positive direction and is fixed with a certain force imparted to fluid bag BS, (2) then, after a lapse of a certain period of time in the above state (1), force sensor P is moved by 1 cm in the Y-axis positive direction (Y1 direction) by movement of rail 25, and (3) then, after a lapse of a certain period of time in the above state (2), force sensor P is moved by 1 cm in the Y-axis negative direction (Y2 direction) by movement of rail 25.

Figure 11:
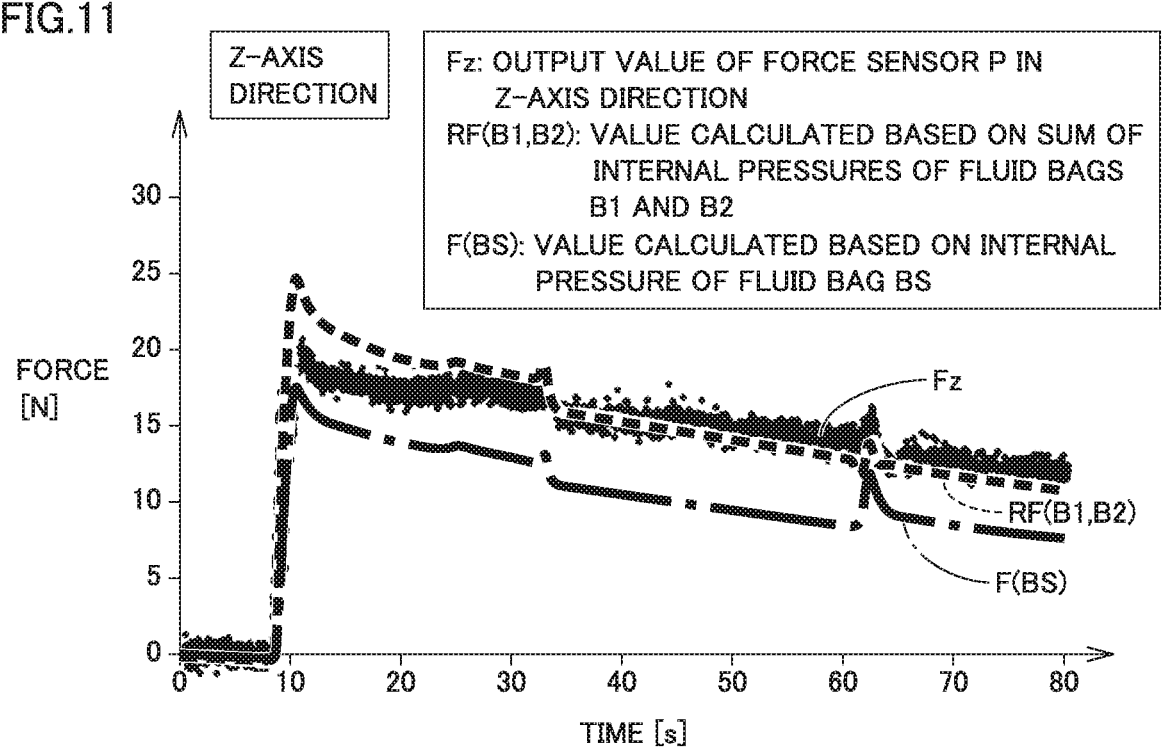
FIG. 11 is a graph showing a relationship between time and force obtained during a predetermined operation for a Z-axis direction in Verification Experiment 1 of an example embodiment of the present invention.

FIG. 11 is a graph showing a relationship between time and force obtained during the above operations of (1) to (3) for the Z-axis direction in Verification Experiment 1 of the present example embodiment. Fz is an output value in the Z-axis direction obtained from force sensor P during the above operations of (1) to (3), RF (B1, B2) is a value calculated based on the sum of the internal pressures of fluid bags B1 and B2 (above expression (B)), and F (BS) is a value calculated based on the internal pressure of fluid bag BS (value detected by pressure sensor S). It is found as shown in FIG. 11 that in the Z-axis direction, the value calculated based on the sum of the internal pressures of fluid bags B1 and B2 has a waveform close to that of the output value of force sensor P in the Z-axis direction.

Figure 12:
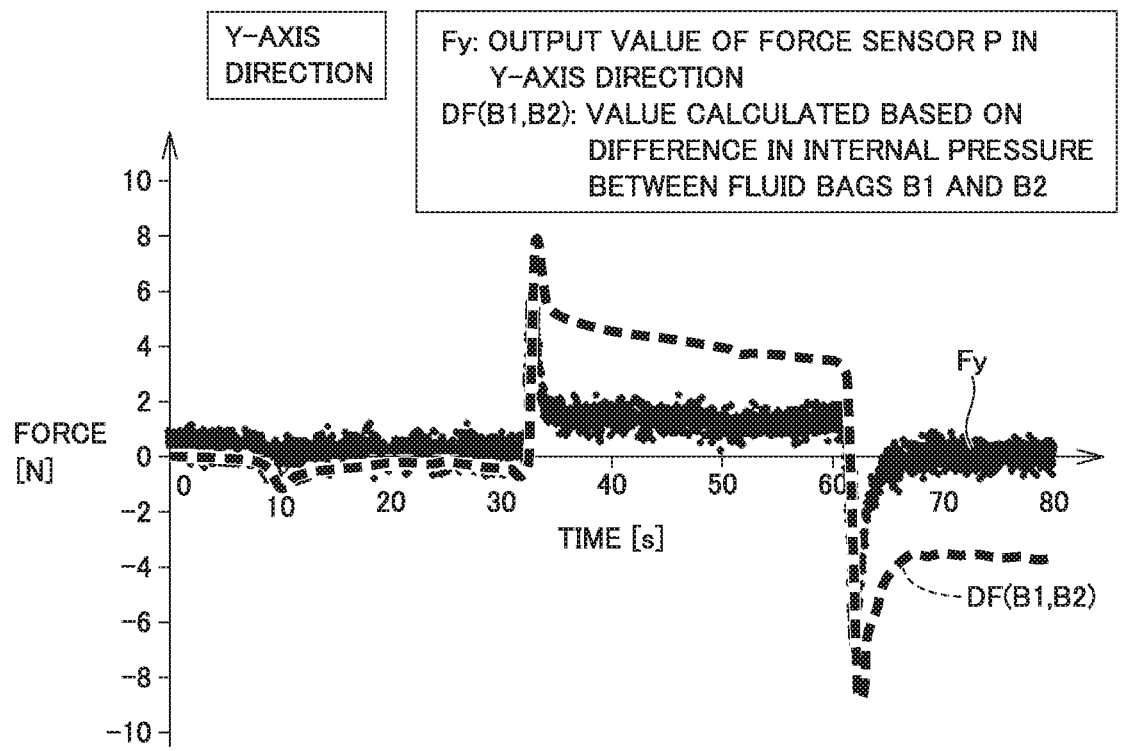
FIG. 12 is a graph showing a relationship between time and force obtained during a predetermined operation for a Y-axis direction in Verification Experiment 1 of an example embodiment of the present invention.

FIG. 12 is a graph showing a relationship between time and force obtained during the above operations of (1) to (3) for the Y-axis direction in Verification Experiment 1 of the present example embodiment. Fy is an output value in the Y-axis direction obtained from force sensor P during the above operations (1) to (3), and DF (B1, B2) is a value calculated based on the difference in the internal pressure between fluid bags B1 and B2 (above expression (C)). It is found as shown in FIG. 12 that in the Y-axis direction, the value calculated based on the difference in the internal pressure between fluid bags B1 and B2 has a waveform close to that of the output value of force sensor P in the Y-axis direction.

Verification Experiment 2

As shown in FIG. 12, for the Y-axis direction, a certain degree of deviation is caused between the value calculated based on the difference in the internal pressure between fluid bags B1 and B2 and the output value of force sensor P. For example, the output value (Fy) of force sensor P is zero from about 65 [s], whereas it is about −4 [N] at DF (B1, B2).

Figure 13:
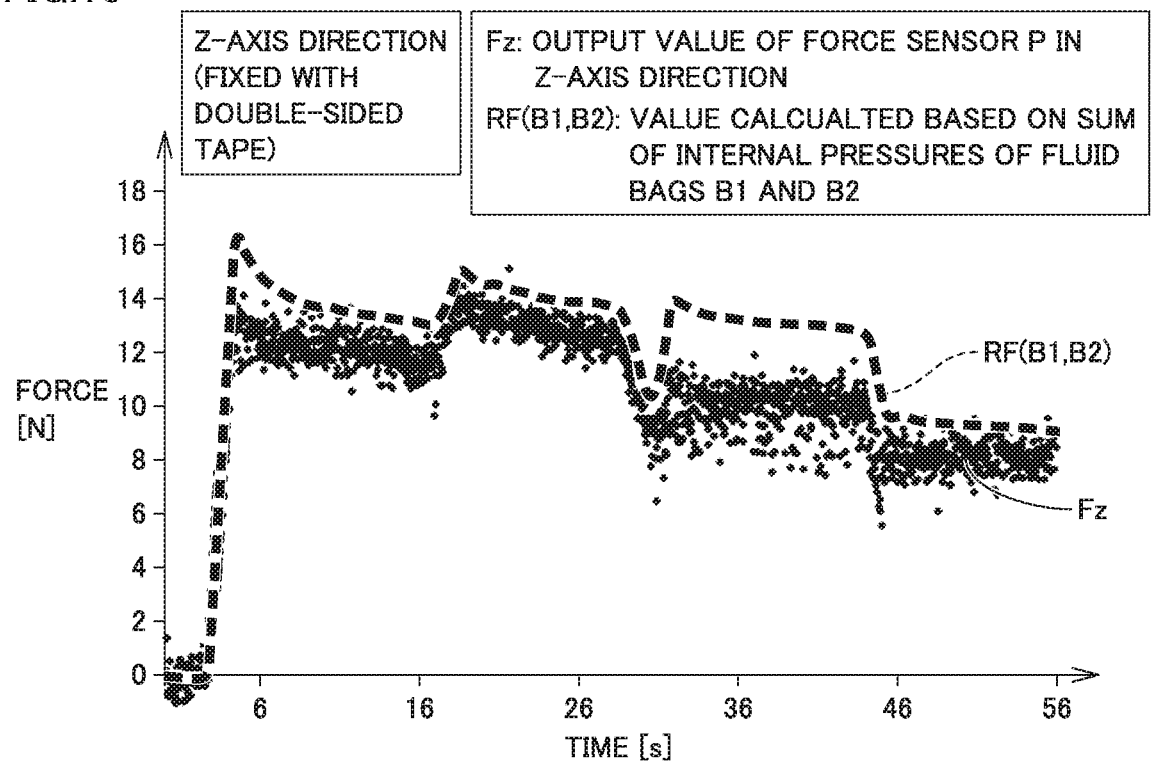
FIG. 13 is a graph showing a relationship between time and force obtained during a predetermined operation for the Z-axis direction in Verification Experiment 2 of an example embodiment of the present invention.
Figure 14:
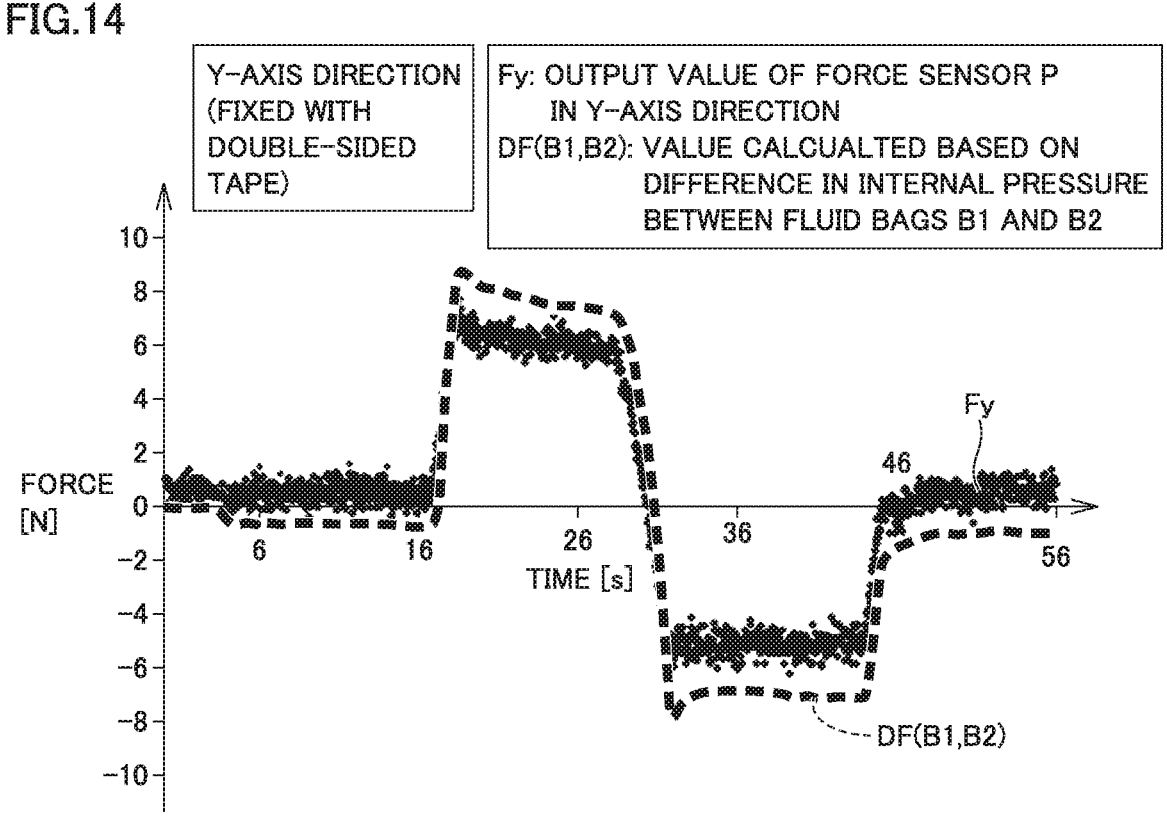
FIG. 14 is a graph showing a relationship between time and force obtained during a predetermined operation for the Y-axis direction in Verification Experiment 2 of an example embodiment of the present invention.

It was surmised that a deviation in the Y-axis direction described above was caused by a slide generated between force sensor P and fluid bag BS when force sensor P was moved in the Y-axis direction. Thus, a double-sided tape was provided on the upper surface (the surface defining contact surface CS) of fluid bag BS to prevent a sliding, and then, an experiment was performed as described above. FIGS. 13 and 14 show the results thereof.

FIG. 13 is a graph showing a relationship between time and force obtained during the above operations of (1) to (3) for the Z-axis direction in Verification Experiment 2 of the present example embodiment. It is found as shown in FIG. 13 that in the Z-axis direction, the value calculated based on the sum of the internal pressures of fluid bags B1 and B2 has a waveform close to that of the output value of force sensor P in the Z-axis direction.

FIG. 14 is a graph showing a relationship between time and force obtained during the above operations of (1) to (3) for the Y-axis direction in Verification Experiment 2 of the present example embodiment. It is found as shown in FIG. 14 that also in the Y-axis direction, the value calculated based on the difference in the internal pressure between fluid bags B1 and B2 has a waveform close to that of the output value of force sensor P in the Y-axis direction.

Eliminating a slide makes a steady-state deviation in the Y-axis direction smaller in the case of FIG. 14 than in the case of FIG. 12. It is thus found that fluid bag BS (contact body) defining contact surface CS is preferably formed such that the surface of fluid bag BS has a feature of being resistant to sliding against the contact target (object) to the extent possible.

Verification Experiment 3

How the portions at which fluid bags B1, B2, and BS are bonded to each other affect the force detection results has been verified.

In Example Embodiment 1 described above, part of outer peripheral portion N of fluid bag BS which is located in the Y-axis positive direction and part of main front surface portion M of fluid bag B1 (sheet-shaped member 4) are bonded to each other to define bonding portion W1 extending linearly therebetween. Similarly, part of outer peripheral portion N of fluid bag BS which is located in the Y-axis negative direction and part of main front surface portion M of fluid bag B2 (sheet-shaped member 4) are bonded to each other to define bonding portion W2 extending linearly therebetween. That is to say, the opposite ends in the Y direction of fluid bag BS are respectively bonded to the central portions of fluid bags B1 and B2.

Figure 15:
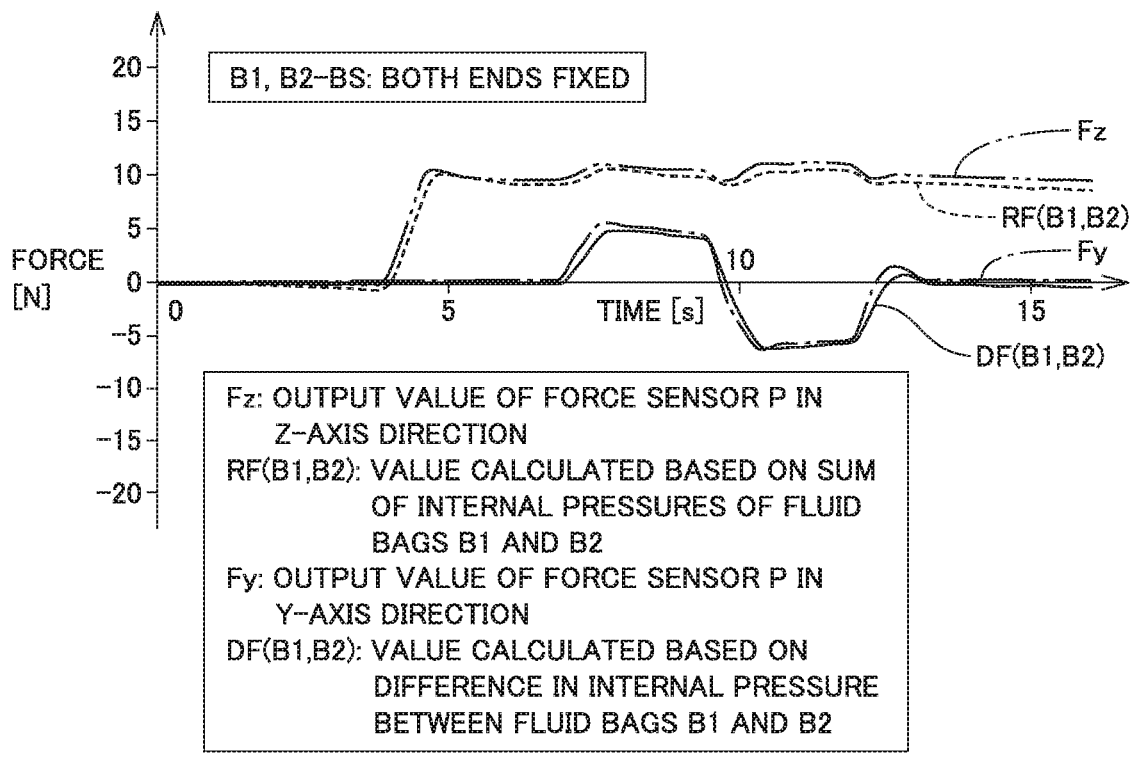
FIG. 15 is a graph showing a relationship between time and force obtained during a predetermined operation for Verification Experiment 3 (both ends fixed) of an example embodiment of the present invention.
Figure 16:
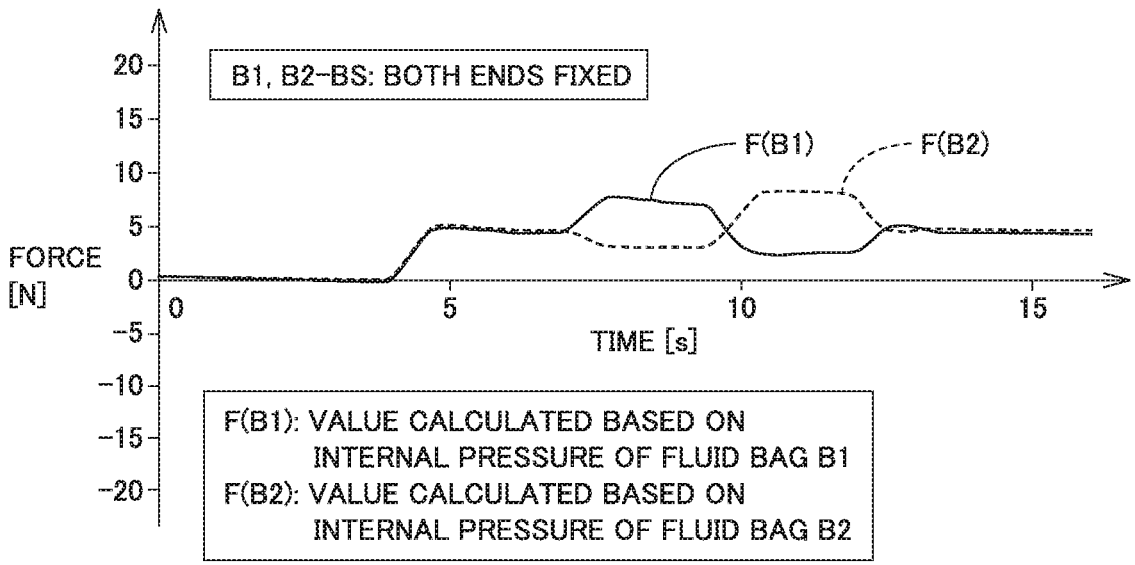
FIG. 16 is another graph showing a relationship between time and force obtained during a predetermined operation for Verification Experiment 3 (both ends fixed) of an example embodiment of the present invention.

The initial pressures of fluid bags B1 and B2 were respectively set to 5.26 kPa and 5.74 kPa in this configuration (hereinafter, also referred to as "both ends fixed"), and a verification experiment similar to that described above was performed. That is to say, a force (9.8 N) in the normal direction was imparted to contact surface CS through force sensor P from 5 [s], and a force in the tangential direction was imparted to contact surface CS from 13 [s] (an amount of movement: ±10 mm). FIGS. 15 and 16 show the experimental results.

Figure 17:
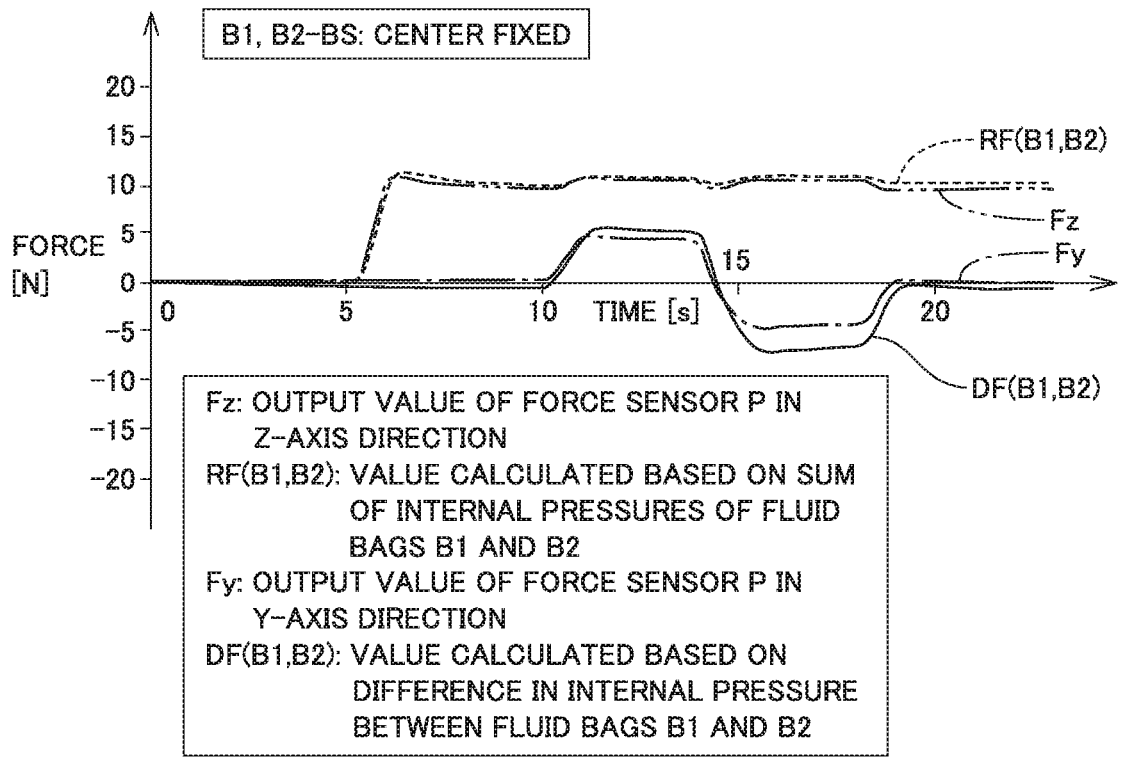
FIG. 17 is a graph showing a relationship between time and force obtained during a predetermined operation for Verification Experiment 3 (center fixed) of an example embodiment of the present invention.
Figure 18:
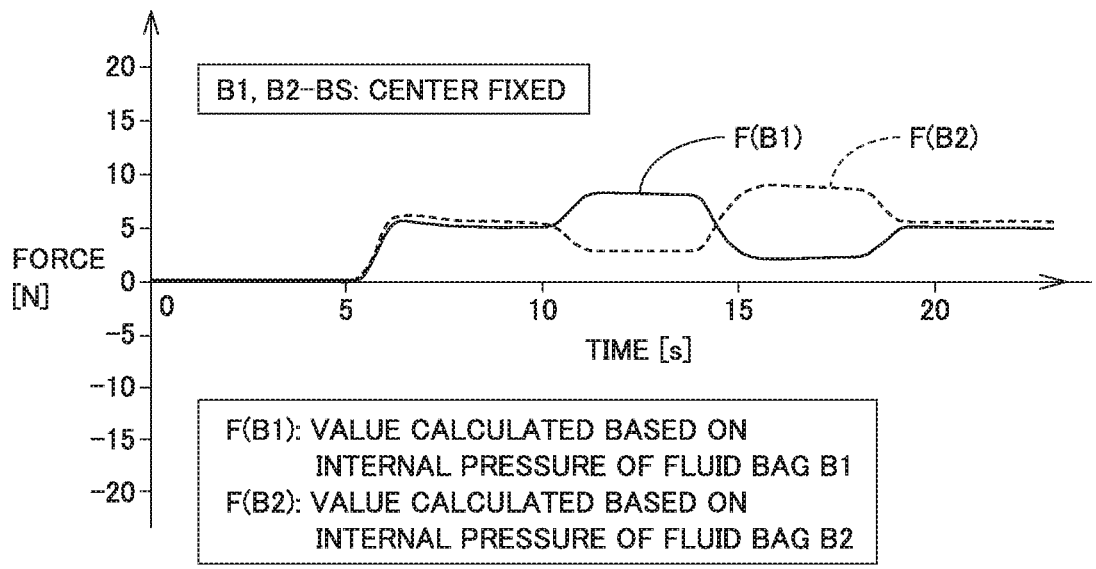
FIG. 18 is another graph showing a relationship between time and force obtained during a predetermined operation for Verification Experiment 3 (center fixed) of an example embodiment of the present invention.

Meanwhile, as another configuration (hereinafter, also referred to as "center fixed"), the central portion of main front surface portion M of fluid bag BS was bonded to the portion (bonding portion W12) at which fluid bag B1 and fluid bag B2 are bonded to each other. The initial pressures of fluid bags B1 and B2 were respectively set to 5.04 kPa and 5.28 kPa in the above configuration, and a verification experiment similar to that described above was performed. That is to say, a force (9.8 N) in the normal direction was imparted to contact surface CS through force sensor P from 5 [s], and a force in the tangential direction was imparted to contact surface CS from 13 [s] (an amount of movement: ±10 mm). FIGS. 17 and 18 show the experimental results.

The comparison of FIGS. 15 to 18 shows that a value calculated based on the internal pressure has a waveform closer to that of the output value of force sensor P in both ends fixed than in center fixed. The reason for this is conceivable that effects of a twist and a deviation are smaller, and particularly when a force is applied in the normal direction, a deviation is caused less easily in the contact of fluid bag BS with fluid bags B1 and B2 in both ends fixed than in center fixed (see FIGS. 16 and 18). It can thus be said that adoption of both ends fixed may be more preferable than the center fixed in order to obtain higher detection accuracy.

Example Embodiment 2

Figure 19:
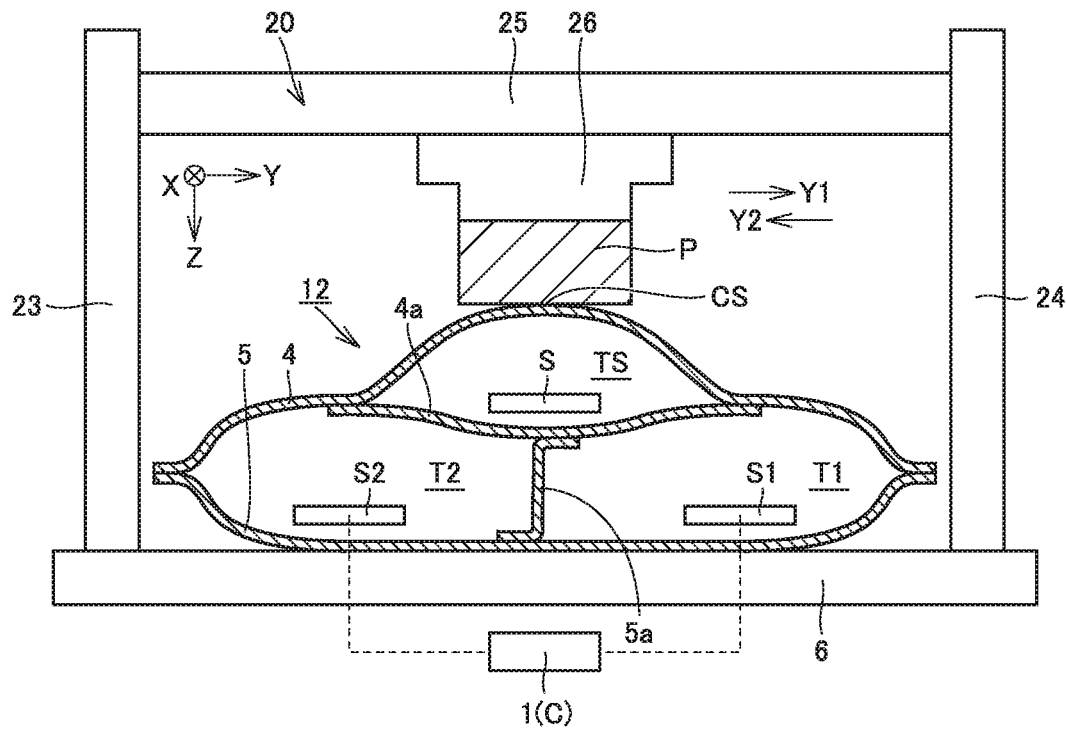
FIG. 19 is a sectional view of a force detector 12 in Example Embodiment 2 of the present invention.

FIG. 19 is a sectional view of a force detector 12 in Example Embodiment 2. FIG. 19 corresponds to FIG. 9 in Example Embodiment 1.

As described also in Example Embodiment 1, the "contact portion", the "first fluid container", and the "second fluid container" can be adjacent to each other by partitioning the internal space of one fluid bag or one or more fluid bags. As shown in FIG. 19, force detector 12 uses large sheet-shaped members 4 and 5 compared with Example Embodiment 1. Disposing sheet-shaped members 4a and 5a therein forms three spaces TS, T1, and T2 substantially as in Example Embodiment 1.

In the present example embodiment, the portions of sheet-shaped members 4 and 4a which partition space TS correspond to the "contact portion", the portions of sheet-shaped members 4, 4a, 5, and 5a which partitions space T1 correspond to the "first fluid container", and the portions of sheet-shaped members 4, 4a, 5, and 5a which partition space T2 correspond to the "second fluid container". This configuration can also detect the force acting on contact surface CS in the tangential direction substantially as in Example Embodiment 1.

Example Embodiment 3

Figure 20:
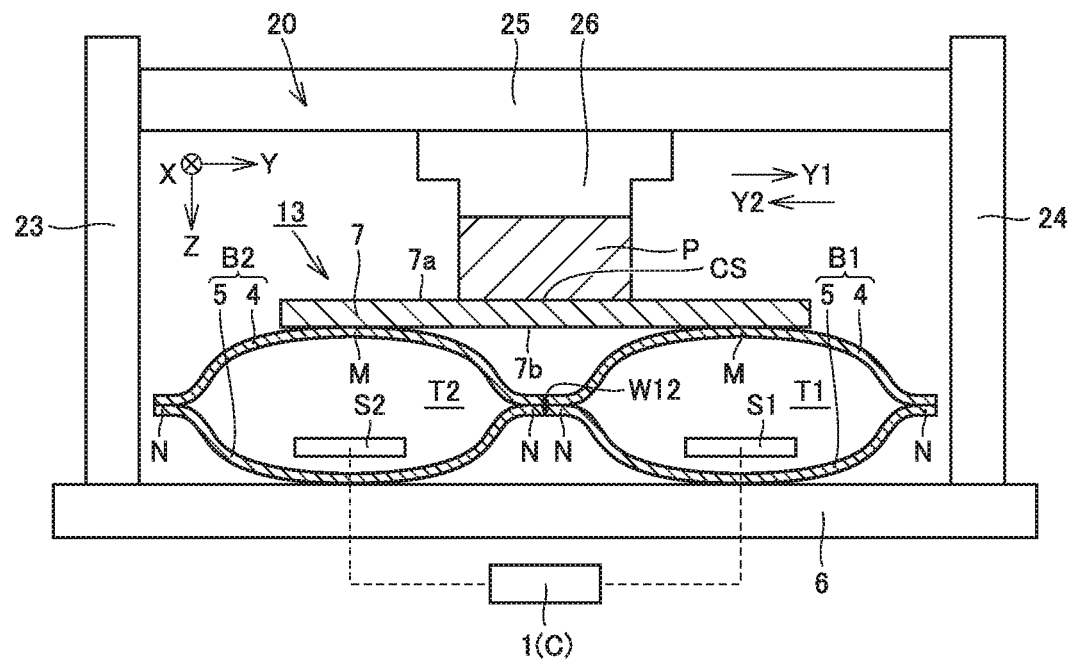
FIG. 20 is a sectional view of a force detector 13 in Example Embodiment 3 of the present invention.

FIG. 20 is a sectional view of a force detector 13 in Example Embodiment 3. FIG. 20 corresponds to FIG. 9 in Example Embodiment 1.

As described also in Example Embodiment 1, it is not necessarily required that the "contact portion" be defined by fluid bag BS. The contact portion in Example Embodiment 3 is defined by a plate-shaped member 7 having a flat plate shape. A front surface 7a and a rear surface 7b of plate-shaped member 7 each have a flat plate shape, and rear surface 7b of plate-shaped member 7 is bonded to sheet-shaped member 4 of each of fluid bags B1 and B2.

Figure 21:
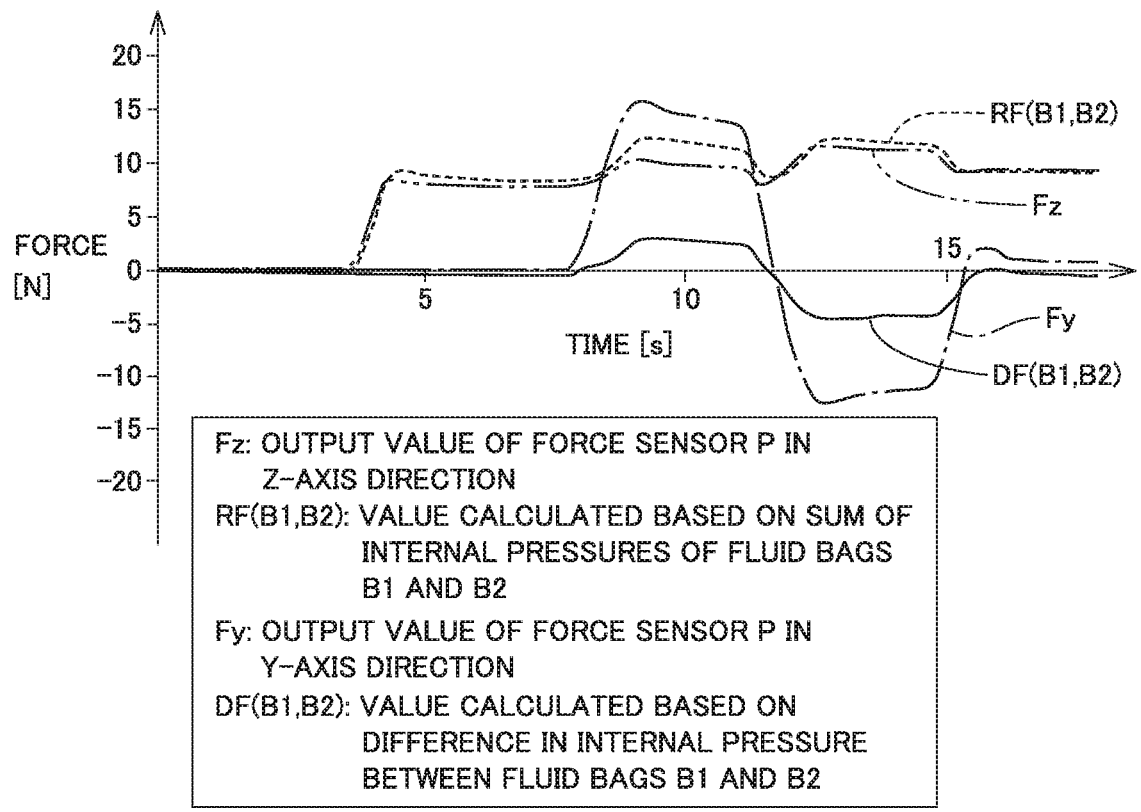
FIG. 21 is a graph for illustrating the function and effect of force detector 13 in Example Embodiment 3 of the present invention.

The initial pressures of fluid bags B1 and B2 were respectively set to 5.72 kPa and 5.52 kPa in force detector 13 having the above configuration, and a verification experiment similar to that described above was performed. That is to say, a force (9.8 N) in the normal direction was imparted to contact surface CS through force sensor P from 5 [s], and a force in the tangential direction was imparted to contact surface CS from 13 [s] (an amount of movement: ±10 mm). FIG. 21 shows the experimental results.

It is found as shown in FIG. 21 that for the normal direction (Z-axis direction), the value calculated based on the sum of the internal pressures of fluid bags B1 and B2 (above expression (B)) has a waveform close to that of the output value of force sensor P in the Z-axis direction. It is found that for the normal direction (Y-axis direction), though an accuracy higher than that of the results described and shown in Example Embodiment 1 and FIG. 15 cannot be obtained, the value calculated based on the difference in the internal pressure between fluid bags B1 and B2 (above expression (C)) has a waveform somewhat relevant to that of the output value of force sensor P in the Y-axis direction. It can thus be said that the use of fluid bag BS may be more preferable than plate-shaped member 7 as the contact portion in order to obtain higher detection accuracy.

Example Embodiment 4

Figure 22:
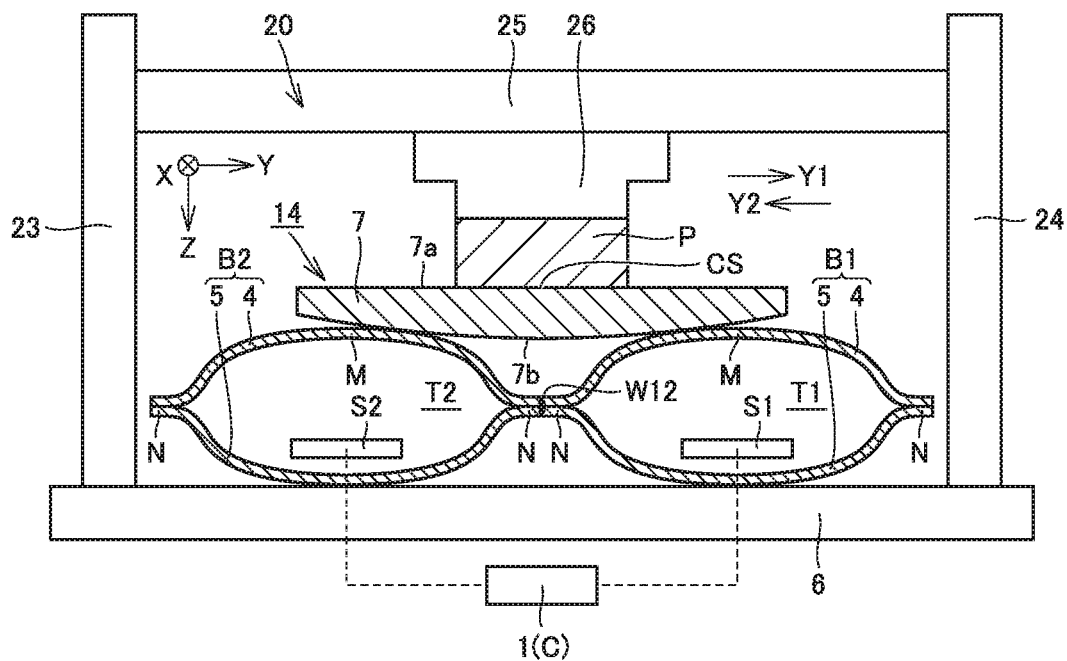
FIG. 22 is a sectional view of a force detector 14 in Example Embodiment 4 of the present invention.

FIG. 22 is a sectional view of a force detector 14 in Example Embodiment 4. FIG. 22 corresponds to FIG. 9 in Example Embodiment 1.

When plate-shaped member 7 as described in Example Embodiment 3 is used as the contact portion, rear surface 7b of plate-shaped member 7 may be shaped into a curved surface to project toward fluid bags B1 and B2. This configuration may be more likely to cause a difference in the internal pressure between fluid bags B1 and B2 due to rear surface 7b having a curved surface shape when a force in the tangential direction is generated, and accordingly, improvement in force detection accuracy is expected.

Verification Experiment 4

Figure 23:
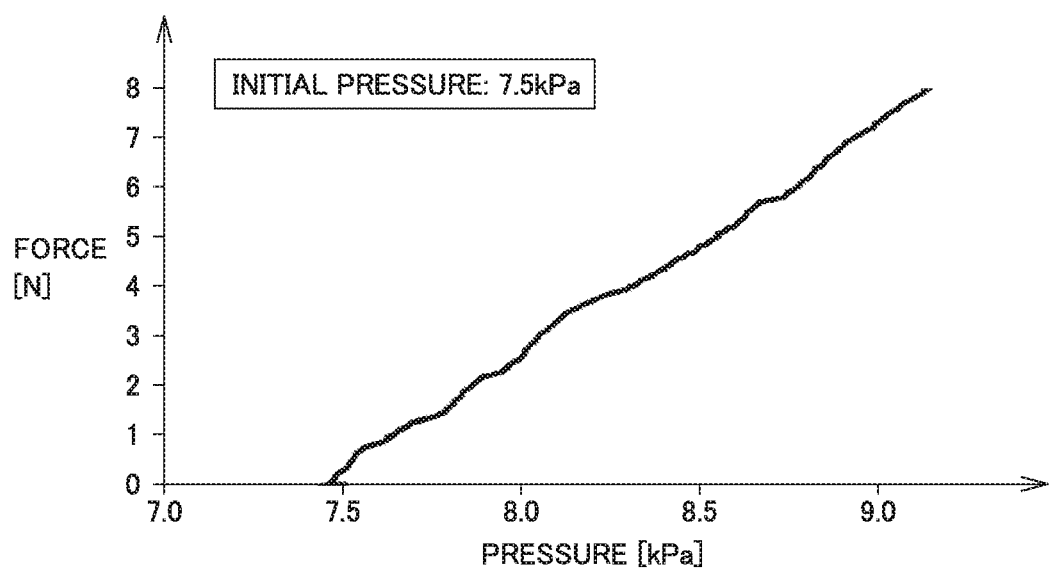
FIG. 23 is a graph showing a relationship between pressure and force when an initial pressure is set to 7.5 kPa for Verification Experiment 4 of an example embodiment of the present invention.
Figure 24:
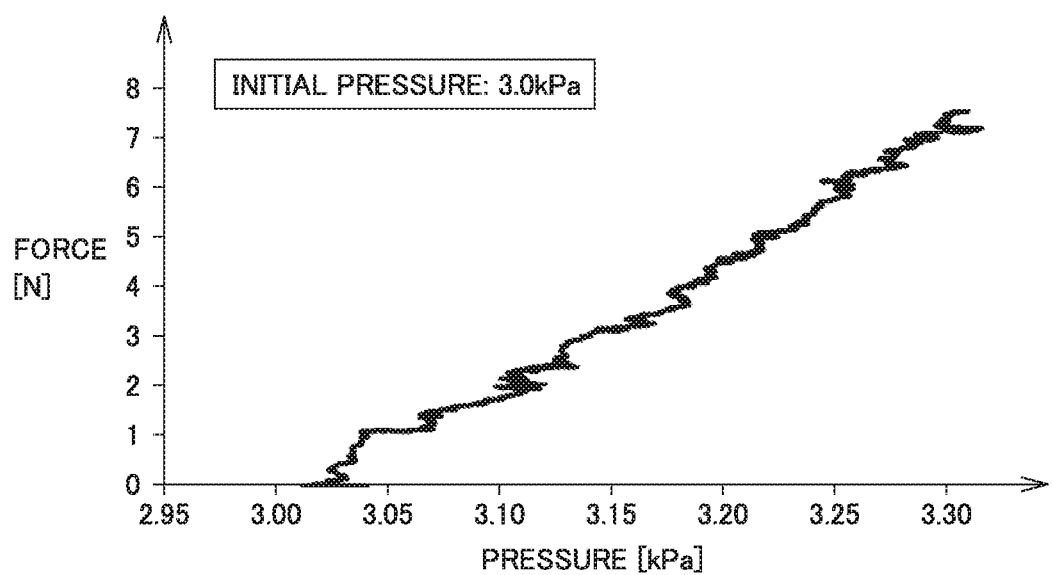
FIG. 24 is a graph showing a relationship between pressure and force when an initial pressure is set to 3.0 kPa for Verification Experiment 4 of an example embodiment of the present invention.

The material for the member of fluid bags BS, B1, and B2 was changed from polyethylene to rubber (rubber balloon), and a pressure-force relationship was verified. FIG. 23 is a graph showing a pressure-force relationship when the initial pressure was set to 7.5 kPa. FIG. 24 is a graph showing a pressure-force relationship when the initial pressure was set to 3.0 kPa.

The results shown in FIGS. 23 and 24 indicate that when the member of fluid bags BS, B1, and B2 is a flexible material (e.g., rubber), increasing the internal pressure of the fluid bag inflates the fluid bag (balloon), making it difficult to maintain a high-pressure state. It can thus be said that hard polyethylene is more suitable than flexible rubber to generate a sufficient difference between the internal pressures of fluid bags BS, B1, and B2.

When the member of fluid bags BS, B1, and B2 is a flexible material (e.g., rubber), a balance is difficult to achieve between contractile force and internal pressure. Thus, hard polyethylene is more suitable than flexible rubber for improving, for example, robustness by setting a target pressure for the internal pressures of fluid bags BS, B1, and B2 and temporarily regulating the pressure values thereof within a certain range.

When the member of fluid bags BS, B1, and B2 is a flexible material (e.g., rubber), the fluid bag has a smaller thickness upon inflation of the fluid bag, which easily varies the change in internal pressure. It can thus be said that hard polyethylene is more suitable than flexible rubber for reducing the variations in the change in the internal pressure of fluid bags BS, B1, and B2 to improve detection accuracy.

Example Embodiment 5

Figure 25:
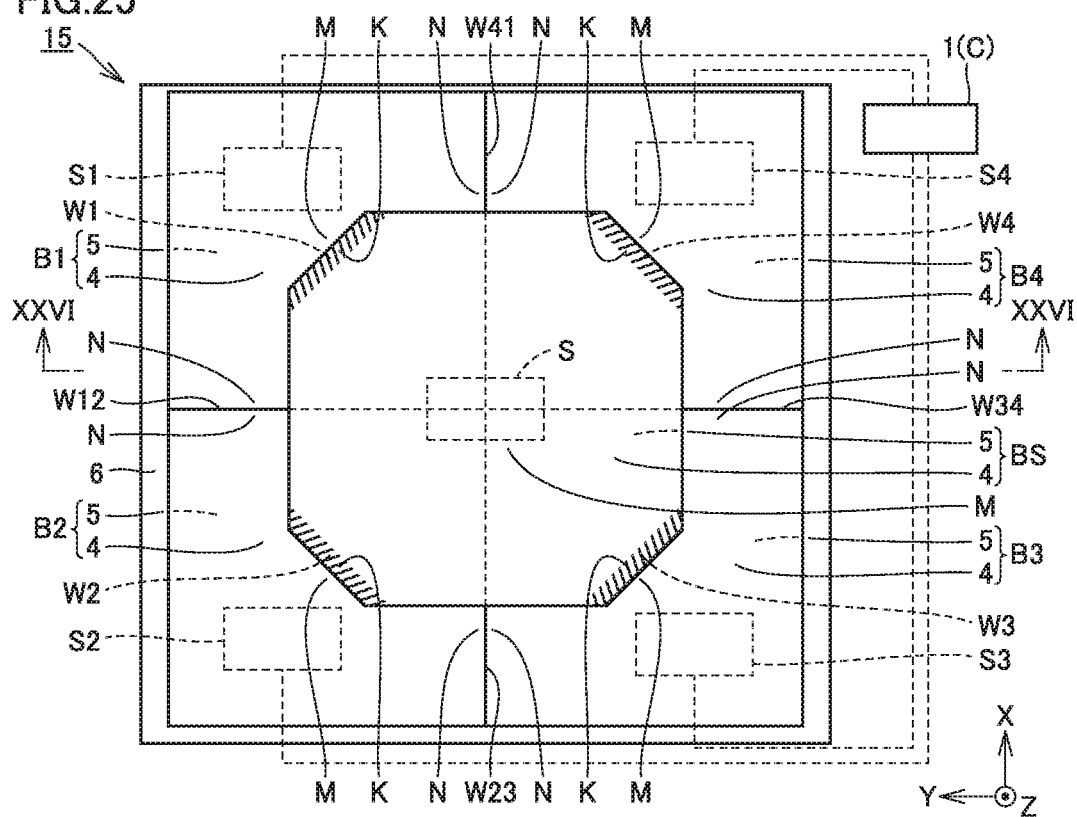
FIG. 25 is a plan view of a force detector 15 in Example Embodiment 5 of the present invention.
Figure 26:
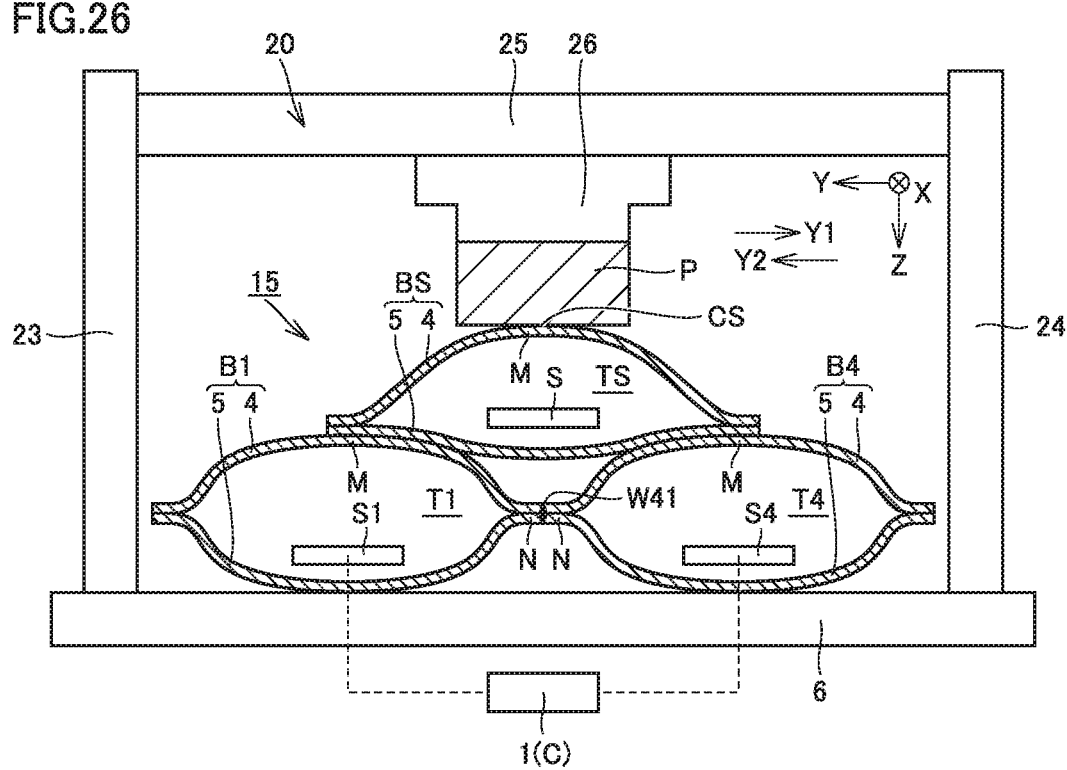
FIG. 26 is a sectional view of force detector 15 and the like in Example Embodiment 5 of the present invention.

A force detector 15 in Example Embodiment 5 will be described with reference to FIGS. 25 to 29. FIG. 25 is a plan view of force detector 15. FIG. 26 is a sectional view of force detector 15 and the like, showing a cross-section taken along a line XXVI-XXVI in FIG. 25. FIG. 26 shows verification device 20 for verifying the performance of force detector 15, in addition to force detector 15.

As shown in FIGS. 25 and 26, force detector 15 includes controller 1, fluid bags BS, B1, B2, B3, and B4, support 6, and pressure sensors S1, S2, S3, and S4. Fluid bag BS corresponds to the "contact portion", fluid bag B1 corresponds to the "first fluid container", fluid bag B2 corresponds to the "second fluid container", fluid bag B3 corresponds to the "third fluid container", and fluid bag B4 corresponds to the "fourth fluid container". Pressure sensors S1, S2, S3, and S4 correspond to a "detector configured to detect an internal pressure of the first fluid container, an internal pressure of the second fluid container, an internal pressure of the third fluid container, and an internal pressure of the fourth fluid container".

Fluid bags B1, B2, B3, and B4 have a configuration similar to that of fluid bags BS, B1, and B2 in each of the above example embodiments. In contrast, fluid bag BS has an octagonal shape in plan view and has a surface area slightly larger than that of each of fluid bags B1, B2, B3, and B4.

Fluid bags B1 and B4 are adjacent to each other in the Y-axis direction, and also, fluid bags B2 and B3 are adjacent to each other in the Y-axis direction. In contrast, fluid bags B1 and B2 are adjacent to each other in the X-axis direction, and also, fluid bags B3 and B4 are adjacent to each other in the X-axis direction.

Outer peripheral portions N of fluid bags B1, B2, B3, and B4 are bonded to each other using a bonding method or material such as welding or an adhesive. Bonding portions W12, W23, W34, and W41 extending linearly are located between outer peripheral portions N. First to fourth fluid containers and contact portions can be adjacent to each other by partitioning the internal space of one fluid bag or one or more fluid bags, as in Example Embodiment 2 described above.

Fluid bag BS is disposed opposite to the side on which fluid bags B1, B2, B3, and B4 are in contact with support 6 and is provided to be adjacent to all of fluid bags B1, B2, B3, and B4. The contact portion can be defined by plate-shaped member 7 as in Example Embodiment 3 described above.

Part of outer peripheral portion N of fluid bag BS defining the contact portion, specifically, four corners K of outer peripheral portion N, and parts of main front surface portions M of sheet-shaped members 4 defining fluid bags B1, B2, B3, and B4 are bonded to each other using bonding methods or material such as welding or an adhesive. Bonding portions W1, W2, W3, and W4 extending linearly are each provided therebetween.

Pressure sensors S1, S2, S3, and S4 are housed in fluid bags B1, B2, B3, and B4, respectively. Pressure sensors S1, S2, S3, and S4 detect the internal pressures of fluid bags B1, B2, B3, and B4 (spaces T1, T2, T3 (not shown), T4), respectively. Pressure sensors S1, S2, S3, and S4 may be an absolute pressure sensor "2SMPB-01 (pressure measuring range: 30 kPa to 110 kPa)" available from OMRON Corporation.

The formation of bonding portions W1, W2, W3, W4, W12, W23, W34, and W41 restrains fluid bags BS, B1, B2, B3, and B4 each other. When an external force is applied to fluid bag BS (contact portion) from an object, the external force applied to fluid bag BS (contact portion) from the object is imparted to all of fluid bags B1 to B4 (first to fourth fluid containers) through fluid bag BS (contact portion).

When a shear force is generated due to the application of a force in the Y-axis direction from above fluid bag BS, one of the contact force (shear force) between fluid bags BS and B1 and the contact force (shear force) between fluid bags BS and B4 increases and the other contact force decreases, causing a difference in internal pressure between fluid bags B1 and B4. Alternatively, when a shear force is generated due to the application of the force in the Y-axis direction from above fluid bag BS, one of the contact force (shear force) between fluid bags BS and B2 and the contact force (shear force) between fluid bags BS and B3 increases and the other contact force decreases, causing a difference in internal pressure between fluid bags B2 and B3.

When a shear force is generated due to the application of the force in the X-axis direction from above fluid bag BS, one of the contact force (shear force) between fluid bags BS and B1 and the contact force (shear force) between fluid bags BS and B2 increases and the other contact force decreases, causing a difference in internal pressure between fluid bags B1 and B2. Alternatively, when a shear force is generated due to the application of the force in the X-axis direction from above fluid bag BS, one of the contact force (shear force) between fluid bags BS and B3 and the contact force (shear force) between fluid bags BS and B4 increases and the other contact force decreases, causing a difference in internal pressure between fluid bags B3 and B4.

Computer C of controller 1 obtains information regarding the internal pressures of fluid bags B1 to B4 from the detector (pressure sensors S1 to S4) and, when an external force is applied to the contact portion (fluid bag BS) from the object, calculates the force acting on contact surface CS between the object and the contact portion in the tangential direction (X-axis direction and Y-axis direction).

That is to say, the configuration having fluid bag BS and four fluid bags B1 to B4, such as force detector 15, can respectively obtain forces Fx, Fy, and Fz in the X, Y, and Z-axis directions using internal pressures P1 to P4 of fluid bags B1 to B4 from expressions (D), (E), and (F) below.

$$Fx:(P1+P4)-(P2+P3) \tag{D}$$

$$Fy:(P1+P2)-(P3+P4) \tag{E}$$

$$Fz: P1+P2+P3+P4 \tag{F}$$

In the above expression (D), (P1+P4) corresponds to a "first internal pressure", and (P2+P3) corresponds to a "second internal pressure". In the above expression (E), (P1+P2) corresponds to the "first internal pressure", and (P3+P4) corresponds to the "second internal pressure". When an external force is applied to the contact portion (fluid bag BS) from the object, computer C calculates the force acting on contact surface CS in the tangential direction based on the difference between the first internal pressure and the second internal pressure.

Verification Experiment 5

An experiment for verifying the performance of force detector 15 described above will now be described. Verification device 20 (FIG. 26) used in the experiment has a configuration similar to that of each of the above example embodiments. A silicon sheet is disposed between fluid bag BS and force sensor P to prevent a slide therebetween, and also, a silicon sheet is disposed between fluid bags B1 to B4 and support 6 to prevent a slide therebetween.

Figure 27:
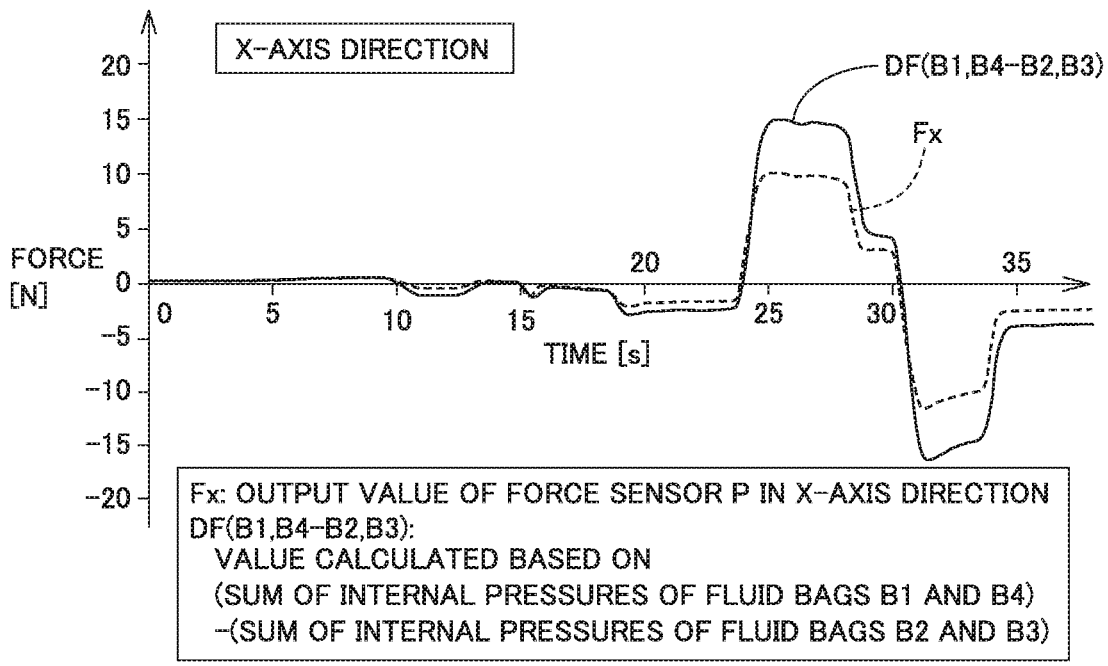
FIG. 27 is a graph showing a relationship between time and force obtained during a predetermined operation for an X-axis direction in Verification Experiment 5 of an example embodiment of the present invention.

FIG. 27 is a graph showing a relationship between time and force obtained during a predetermined operation for the X-axis direction in Verification Experiment 5 of the present example embodiment. Fx is an output value in the X-axis direction obtained from force sensor P during the predetermined operation, and DF (B1, B4-B2, B3) is a value calculated based on ((sum of internal pressures of fluid bags B1 and B4)−(sum of internal pressures of fluid bags B2 and B3)). It is found as shown in FIG. 27 that in the X-axis direction, the value calculated based on ((sum of internal pressures of fluid bags B1 and B4)−(sum of internal pressures of fluid bags B2 and B3)) has a waveform close to that of the output value of force sensor P in the X-axis direction.

Figure 28:
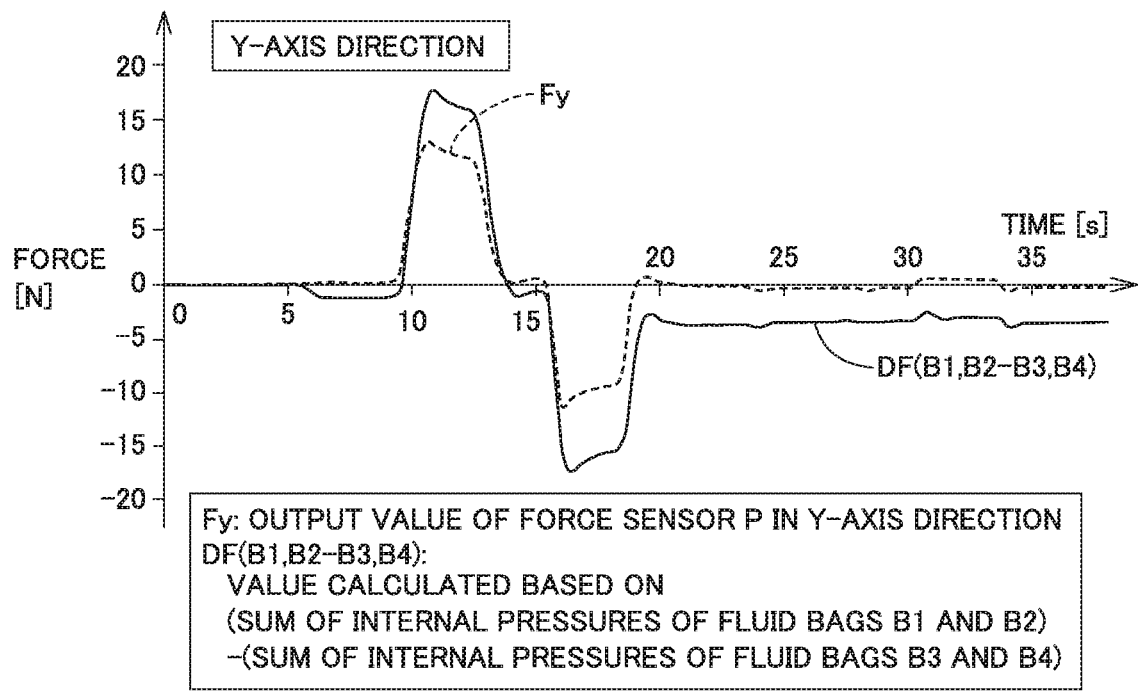
FIG. 28 is a graph showing a relationship between time and force obtained during a predetermined operation for the Y-axis direction in Verification Experiment 5 of an example embodiment of the present invention.

FIG. 28 is a graph showing a relationship between time and force obtained during a predetermined operation for the Y-axis direction in Verification Experiment 5 of the present example embodiment. Fy is an output value in the Y-axis direction obtained from force sensor P during a predetermined operation, and DF (B1, B2-B3, B4) is a value calculated based on ((sum of internal pressures of fluid bags B1 and B2)−(sum of internal pressures of fluid bags B3 and B4)). It is found as shown in FIG. 28 that also in the Y-axis direction, the value calculated based on ((sum of internal pressures of fluid bags B1 and B2)−(sum of internal pressures of fluid bags B3 and B4)) has a waveform close to that of the output value of force sensor P in the Y-axis direction.

Figure 29:
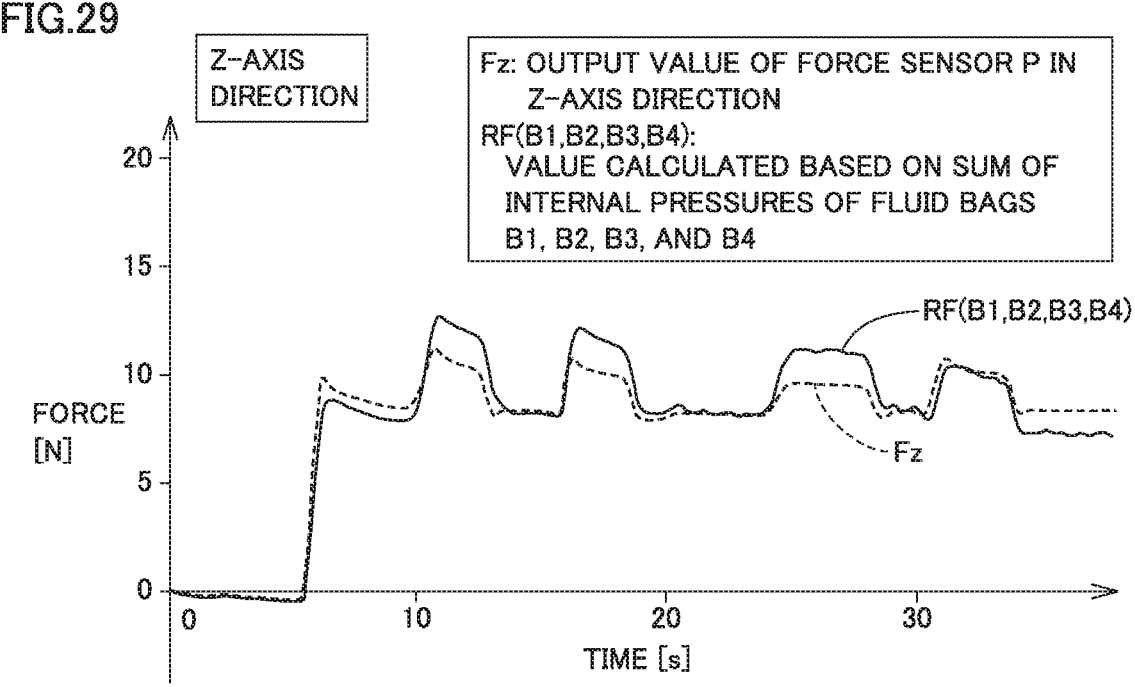
FIG. 29 is a graph showing a relationship between time and force obtained during a predetermined operation for the Z-axis direction in Verification Experiment 5 of an example embodiment of the present invention.

FIG. 29 is a graph showing a relationship between time and force obtained during a predetermined operation for the Z-axis direction in Verification Experiment 5 of the present example embodiment. Fz is an output value in the Z-axis direction obtained from force sensor P during a predetermined operation, and RF (B1, B2, B3, B4) is a value calculated based on (fluid bags B1, B2, B3, B4). It is found as shown in FIG. 29 that in the Z-axis direction, a value calculated based on (fluid bags B1, B2, B3, B4) has a waveform close to that of the output value of force sensor P in the Z-axis direction.

Verification Experiment 6

Each of fluid bag B1 (first fluid container) and fluid bag B2 (second fluid container) used in the example embodiments and verification experiments described above has a bag shape defined by the outer peripheral portions of two sheet-shaped members 4 and 5 which are bonding to each other. Sheet-shaped members 4 and 5 have the same size and shape, 100 mm×100 mm, and the material therefor is plastic such as polyethylene. In plan view of each of fluid bags B1 and B2 while being contracted, fluid bags B1 and B2 have a square outer shape (see FIG. 7).

In plan view of fluid bag B1 (first fluid container), fluid bag B2 (second fluid container), fluid bag B3 (third fluid container), and fluid bag B4 (fourth fluid container) used in Example Embodiment 5 described above while being contracted, each of fluid bags B1 to B4 has a square outer shape (see FIG. 25).

With reference to FIG. 30, it is conceivable that the shape of a fluid bag may greatly affect sensor characteristics in production of a fluid bag defining and functioning as a main body of the force detector. In particular, parameters such as shape and size are expected to affect, for example, an amount of contraction of a fluid bag upon pressurization of a fluid bag and a degree of a wrinkle caused in the fluid bag (buckling of the outer peripheral portion of the fluid bag) to change sensor characteristics.

Figure 33:
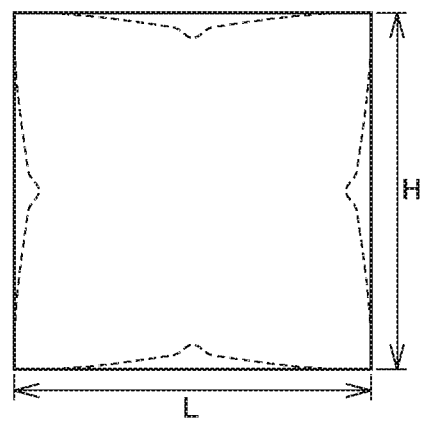
FIG. 33 is a plan view of a fluid bag having a square shape used in Verification Experiment 6 of an example embodiment of the present invention.
Figure 34:
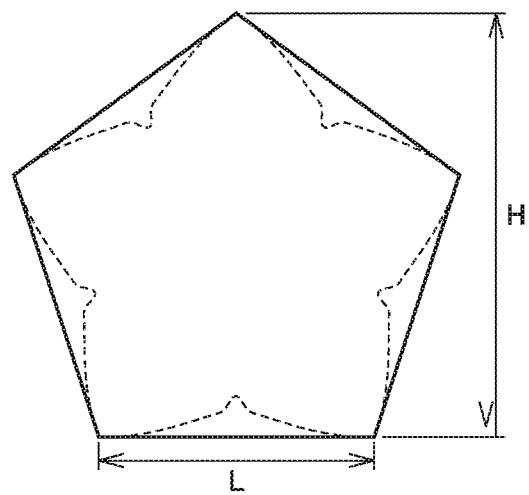
FIG. 34 is a plan view of a fluid bag having a regular pentagon shape used in Verification Experiment 6 of an example embodiment of the present invention.

Verification Experiment 6 has verified how the outer shape of a fluid bag affects the characteristics of a fluid bag sensor from the relationship between the internal pressure of the fluid bag and the external force imparted to the fluid bag. The outer shapes in plan view of the fluid bags used in the experiment are rectangle (FIG. 31), equilateral triangle (FIG. 32), square (FIG. 33), and regular pentagon (FIG. 34). All of these fluid bags were produced from a polyethylene material (LEPE), the initial pressure of the fluid bag was set to 20 [kPa], and a sampling period of various data was set to 5.0 [ms].

Base lengths L [mm] and heights H [mm] of these fluid bags are as shown in FIG. 30. Values of length L and height H of each fluid bag were set such that the surface area is approximately identical in the fluid bags having the respective outer shapes.

With reference to FIGS. 31 to 34, an inelastic sheet was processed into a bag using heat bonding. When the obtained fluid bags are pressurized (herein, at 20 kPa), the central portion of the fluid bag inflates, increasing a thickness T [mm] of the fluid bag. Along with this, the bonded portion provided on the periphery of the fluid bag is pulled inward (see the broken lines in FIGS. 31 to 34).

The comparison of the equilateral triangle (FIG. 32), square (FIG. 33), and regular pentagon (FIG. 34) reveals that a wrinkle (buckling) caused on each side increases with an increasing number of corners of a fluid bag to increase thickness T (FIG. 30). In contrast, for a rectangular (FIG. 31), a wrinkle is mainly caused on the short sides of a rectangular and almost no wrinkle is caused on the long sides of the rectangular as shown in FIG. 31. That is to say, it is revealed that an amount of contraction of the bonded portion and the depth of a wrinkle differ depending on a bag shape. The following measurement experiment was performed to check effects on changes in internal pressure when an external force is imparted to fluid bags having different outer shapes.

Figure 35:
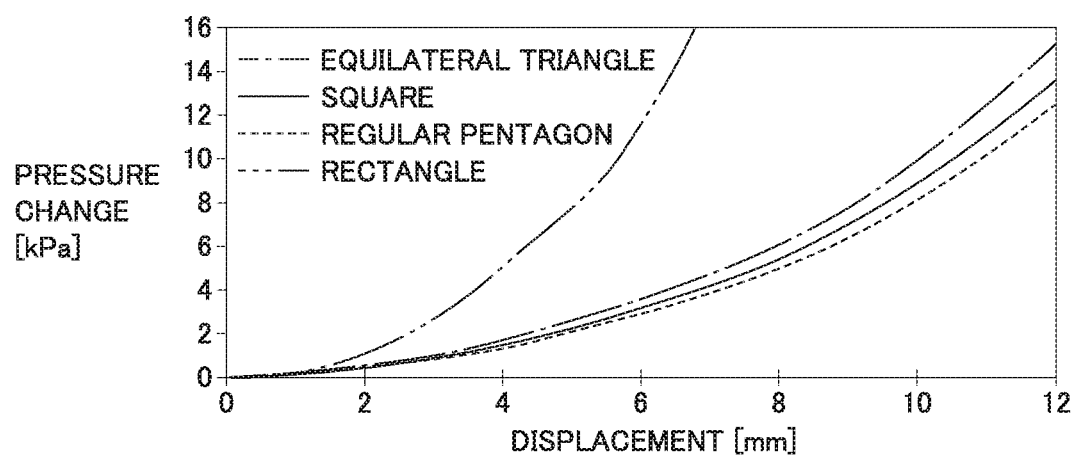
FIG. 35 shows a relationship between a displacement in a main front surface portion of a fluid bag and a change in the internal pressure of the fluid bag for the results of Verification Experiment 6 of an example embodiment of the present invention.

FIG. 35 shows a relationship between a displacement of a main front surface portion of a fluid bag and a change in the internal pressure of the fluid bag. The relationship between displacement and pressure change reveals that a fluid bag having a rectangular outer shape causes pressure changes relative to changes in displacement at high sensitivity compared with another fluid bag.

Figure 36:
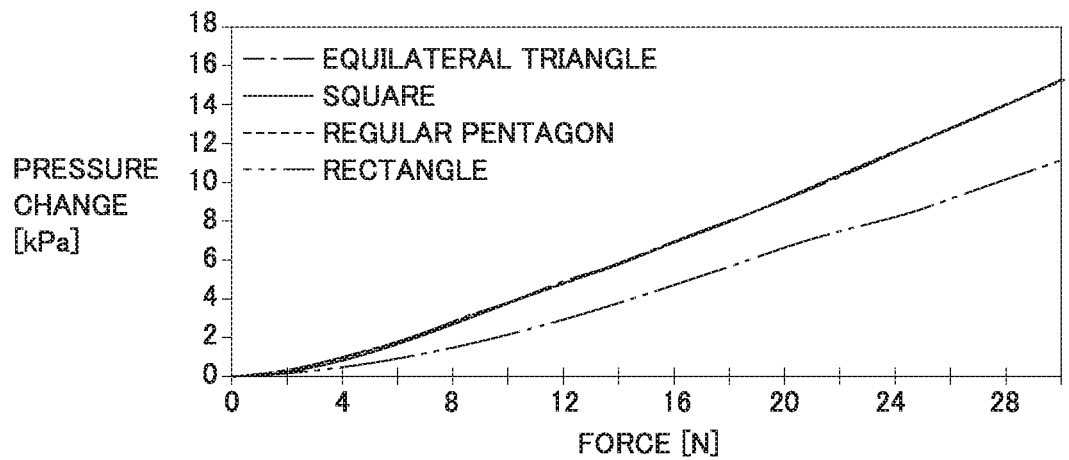
FIG. 36 shows a relationship between an external force imparted to the main front surface portion of the fluid bag and a change in the internal pressure of the fluid bag for the results of Verification Experiment 6 of an example embodiment of the present invention.

FIG. 36 shows a relationship between an external force imparted to a main front surface portion of a fluid bag and a change in the internal pressure of the fluid bag. The relationship between external force and pressure change reveals that a fluid bag having a rectangular outer shape causes pressure changes relative to changes in external force at low sensitivity compared with another fluid bag.

Figure 37:
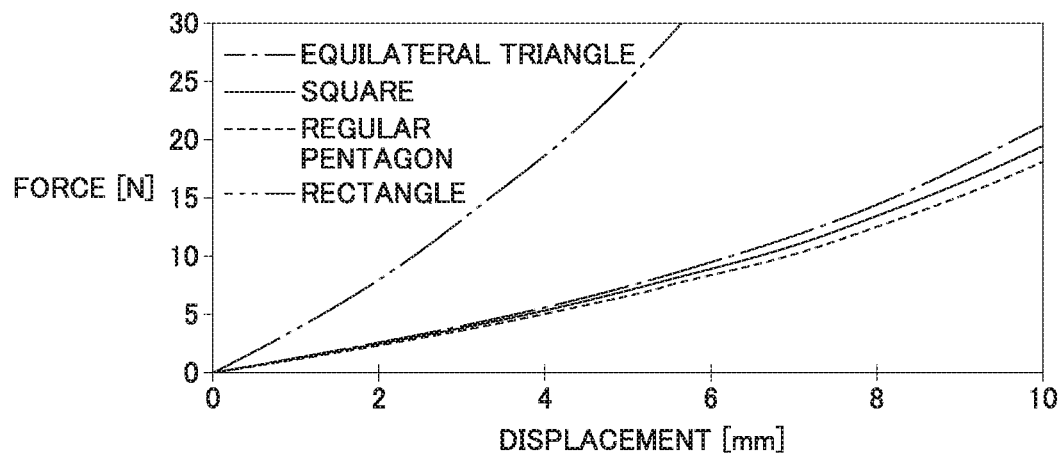
FIG. 37 shows a relationship between a displacement of the main front surface portion of the fluid bag and an external force imparted to the main front surface portion of the fluid bag for the results of Verification Experiment 6 of an example embodiment of the present invention.

FIG. 37 shows a relationship between a displacement of a main front surface portion of a fluid bag and an external force imparted to the main front surface portion of the fluid bag. The comparison among an equilateral triangle, a square, and a regular pentagon reveals that a larger number of corners results in lower rigidity (i.e., reveals that a larger number of corners results in a greater displacement of the main front surface portion of the fluid bag by input with a smaller force), as shown in FIG. 37.

As described above, a larger number of corners results in a deeper wrinkle. A fluid bag with a larger number of corners is more likely to deform to inflate horizontally (deform to restore a wrinkle-free state) by an amount of a deeper wrinkle. It is thus conceivable that for a fluid bag with a larger number of corners, an external force may be canceled by a wrinkle's deformation for restoration even when the external force is applied thereto, and an actual volume change caused inside the fluid bag decreases, reducing a pressure change correspondingly (FIG. 35).

In contrast, for a rectangle, a wrinkle is mainly caused on the short sides of a fluid bag, and almost no wrinkle is caused on the long sides of the fluid bag (see FIG. 31). Thus, when an external force is applied to a fluid bag, a rectangular fluid bag little inflates horizontally, resulting in great pressure changes compared with any other polygonal shape. Moreover, the rectangular fluid bag has a portion that extends longer longitudinally than a fluid bag having any other polygonal shape, and accordingly has a larger contact area from the initial point in time of application of external force. It is thus revealed that rigidly increases (i.e., the main front surface portion of the fluid bag deforms less by an input with the same external force).

Comprehensively considering the above results, it is conceivable that a rectangular fluid bag may be more suitable than any another fluid bag for providing high rigidity to a sensor surface. For example, in the use of a force detector as a massage machine or the like, high rigidity may be utilized. The massage machine may have low rigidity. Meanwhile, the comparison between a regular polygonal fluid bag and a rectangular fluid bag reveals that at the same initial volume, the regular polygonal fluid bag is superior to the rectangular fluid bag in force resolving power. It is also revealed that almost no difference is found in power resolving power among an equilateral triangle, a square, and a regular pentagon.

It is revealed that a regular polygonal fluid bag is better than a rectangular fluid bag when a higher priority is given to the force resolving power. Considering production convenience, a square among regular polygons is especially manageable in terms of, for example, production convenience.

As described above, a fluid bag having a larger number of corners is more likely to deform to inflate horizontally (deform to restore a wrinkle-free state) by an amount of a deeper wrinkle when the fluid bag is pressurized. In order to reduce or prevent a wrinkle caused in the outer peripheral portion of a fluid bag, a reinforcing portion to increase the rigidity of this portion may be provided at the portion at which the outer peripheral portions of sheet-shaped members 4 and 5 are bonded to each other.

The reinforcing portion may be obtained by, for example, applying another resin (e.g., an adhesive) such as epoxy to the outer peripheral portions of sheet-shaped members 4 and 5 to increase the rigidity of the outer peripheral portion by the cured epoxy (reinforcing portion). The reinforcing portion may be a frame-shaped clamp member that clamps the outer peripheral portion of the fluid bag. Attaching the frame-shaped clamp member to the fluid bag so as to caulk the outer peripheral portion of the fluid bag increases the rigidity of the outer peripheral portion of the fluid bag to reduce or prevent the generation of a wrinkle.

The reinforcing member may also be obtained by inwardly folding back the outer peripheral portions of two sheet-shaped members 4 and 5, increasing the rigidity of the outer peripheral portion of the fluid bag, which reduces or prevents the generation of a wrinkle. From the viewpoint of reducing or preventing the generation of a wrinkle, the thicknesses of sheet-shaped members 4 and 5 defining a fluid bag may be increased, or the initial pressure of the fluid bag may be set to a small value.

The above contents of the present disclosure could be summarized as follows.

A force detector according to a first aspect of the present invention includes a support, a first fluid container, a second fluid container, a contact portion, a detector, and a computer. The first fluid container and the second fluid container are supported by the support, have a bag shape defined by a sheet-shaped member, and are adjacent to each other. The contact portion is disposed opposite to a side on which the first fluid container and the second fluid container are in contact with the support and is provided to be adjacent to both the first fluid container and the second fluid container. The detector is configured to detect an internal pressure of the first fluid container and an internal pressure of the second fluid container. The computer is configured or programmed to obtain information regarding the internal pressure of the first fluid container and the internal pressure of the second fluid container from the detector and, upon application of an external force to the contact portion from an object, calculate a force acting in a tangential direction on a contact surface between the object and the contact portion. Upon application of the external force to the contact portion from the object, the external force applied to the contact portion from the object is imparted to both the first fluid container and the second fluid container through the contact portion. Upon application of the external force to the contact portion from the object, the computer calculates the force acting on the contact surface in the tangential direction based on a difference between the internal pressure of the first fluid container and the internal pressure of the second fluid container.

In the force detector, the contact portion is preferably defined by a fluid bag with a fluid contained therein.

In the force detector, preferably, each of the first fluid container and the second fluid container is defined by a fluid bag with a fluid contained therein, and the fluid bag defining the first fluid container, the fluid bag defining the second fluid container, and the fluid bag defining the contact portion are bonded to each other.

In the force detector, preferably, the fluid bag defining the first fluid container, the fluid bag defining the second fluid container, and the fluid bag defining the contact portion each include a main front surface portion and an outer peripheral portion located on an outer periphery of the main front surface portion, and part of the outer peripheral portion of the fluid bag defining the contact portion and part of the main front surface portion of the fluid bag defining each of the first fluid container and the second fluid container are bonded to each other.

In the force detector, preferably, each of the fluid bag defining the first fluid container and the fluid bag defining the second fluid container has a bag shape defined by outer peripheral portions of two of the sheet-shaped members which are bonded to each other, and each of the fluid bags has a polygonal outer shape while being contracted in plan view.

In the force detector, preferably, each of the fluid bag defining the first fluid container and the fluid bag defining the second fluid container has a rectangular outer shape while being contracted in plan view.

In the force detector, preferably, a portion at which the outer peripheral portions of the two sheet-shaped members are bonded to each other is provided with a reinforcing portion to increase rigidity of the portion.

A force detector according to a second aspect of the present invention includes a support, a first fluid container, a second fluid container, a third fluid container, a fourth fluid container, a contact portion, a detector, and a computer. The first fluid container, the second fluid container, the third fluid container, and the fourth fluid container are supported by the support, have a bag shape defined by a sheet-shaped member, and are adjacent to each other. The contact portion is disposed opposite to a side on which the first fluid container, the second fluid container, the third fluid container, and the fourth fluid container are in contact with the support and is provided to be adjacent to all the first fluid container, the second fluid container, the third fluid container, and the fourth fluid container. The detector is configured to detect an internal pressure of the first fluid container, an internal pressure of the second fluid container, an internal pressure of the third fluid container, and an internal pressure of the fourth fluid container. The computer is configured or programmed to obtain information regarding the internal pressure of the first fluid container, the internal pressure of the second fluid container, the internal pressure of the third fluid container, and the internal pressure of the fourth fluid container from the detector and, upon application of an external force to the contact portion from an object, calculate a force acting in a tangential direction on a contact surface between the object and the contact portion. Upon application of the external force to the contact portion from the object, the external force applied to the contact portion from the object is imparted to all the first fluid container, the second fluid container, the third fluid container, and the fourth fluid container through the contact portion. When a sum of internal pressures of two fluid containers of the first fluid container, the second fluid container, the third fluid container, and the fourth fluid container is defined as a first internal pressure and a sum of internal pressures of the other two fluid containers of the first fluid container, the second fluid container, the third fluid container, and the fourth fluid container is defined as a second internal pressure, upon application of the external force to the contact portion from the object, the computer calculates the force acting on the contact surface in the tangential direction based on a difference between the first internal pressure and the second internal pressure.

In the force detector, the contact portion is preferably defined by a fluid bag with a fluid contained therein.

In the force detector, preferably, each of the first fluid container, the second fluid container, the third fluid container, and the fourth fluid container is defined by a fluid bag with a fluid contained therein, and the fluid bag defining the first fluid container, the fluid bag defining the second fluid container, the fluid bag defining the third fluid container, the fluid bag defining the fourth fluid container, and the fluid bag defining the contact portion are bonded to each other.

In the force detector, preferably, the fluid bag defining the first fluid container, the fluid bag defining the second fluid container, the fluid bag defining the third fluid container, the fluid bag defining the fourth fluid container, and the fluid bag defining the contact portion each include a main front surface portion and an outer peripheral portion located on an outer periphery of the main front surface portion, and part of the outer peripheral portion of the fluid bag defining the contact portion and part of the main front surface portion of the fluid bag defining each of the first fluid container, the second fluid container, the third fluid container, and the fourth fluid container are bonded to each other.

In the force detector, preferably, each of the fluid bag defining the first fluid container, the fluid bag defining the second fluid container, the fluid bag defining the third fluid container, and the fluid bag defining the fourth fluid container has a bag shape defined by outer peripheral portions of two of the sheet-shaped members which are bonded to each other, and each of the fluid bags has a polygonal outer shape while being contracted in plan view.

In the force detector, preferably, each of the fluid bag defining the first fluid container, the fluid bag defining the second fluid container, the fluid bag defining the third fluid container, and the fluid bag defining the fourth fluid container has a rectangular outer shape while being in contracted in plan view.

In the force detector, preferably, a portion at which the outer peripheral portions of the two sheet-shaped members are bonded to each other is provided with a reinforcing portion to increase rigidity of the portion.

The above force detector includes a plurality of fluid containers, and accordingly, upon application of an external force to the contact portion from an object, can calculate a force acting on the contact surface in the tangential direction based on a difference in the internal pressure generated between the plurality of fluid containers.

While example embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:
1. A force detector comprising:
 a support;
 a first fluid container and a second fluid container supported by the support, including a bag shape defined by a sheet-shaped member, and disposed adjacent to each other;
 a contact portion disposed opposite to a side on which the first fluid container and the second fluid container are in contact with the support, the contact portion being adjacent to both the first fluid container and the second fluid container;
 a detector configured to detect an internal pressure of the first fluid container and an internal pressure of the second fluid container; and
 a computer configured or programmed to obtain information regarding the internal pressure of the first fluid container and the internal pressure of the second fluid container from the detector and, upon application of an external force to the contact portion from an object, calculate a force acting in a tangential direction on a contact surface between the object and the contact portion; wherein
 upon application of the external force to the contact portion from the object, the external force applied to the contact portion from the object is imparted to both the first fluid container and the second fluid container through the contact portion; and
 upon application of the external force to the contact portion from the object, the computer calculates the force acting on the contact surface in the tangential direction based on a difference between the internal pressure of the first fluid container and the internal pressure of the second fluid container.

2. The force detector according to claim 1, wherein the contact portion is defined by a fluid bag with a fluid contained therein.

3. The force detector according to claim 2, wherein
each of the first fluid container and the second fluid container is defined by a fluid bag with a fluid contained therein; and
the fluid bag defining the first fluid container, the fluid bag defining the second fluid container, and the fluid bag defining the contact portion are bonded to each other.

4. The force detector according to claim 3, wherein
the fluid bag defining the first fluid container, the fluid bag defining the second fluid container, and the fluid bag defining the contact portion each include a main front surface portion and an outer peripheral portion located on an outer periphery of the main front surface portion; and
part of the outer peripheral portion of the fluid bag defining the contact portion and part of the main front surface portion of the fluid bag defining each of the first fluid container and the second fluid container are bonded to each other.

5. The force detector according to claim 3, wherein each of the fluid bag defining the first fluid container and the fluid bag defining the second fluid container has a bag shape defined by outer peripheral portions of two of the sheet-shaped members which are bonded to each other, and each of the fluid bags has a polygonal outer shape while being contracted in plan view.

6. The force detector according to claim 5, wherein each of the fluid bag defining the first fluid container and the fluid bag defining the second fluid container has a rectangular outer shape while being contracted in plan view.

7. The force detector according to claim 5, wherein a portion at which the outer peripheral portions of the two sheet-shaped members are bonded to each other is provided with a reinforcing portion to increase rigidity.

8. A force detector comprising:
a support;
a first fluid container, a second fluid container, a third fluid container, and a fourth fluid container supported by the support, including a bag shape defined by a sheet-shaped member, and disposed adjacent to each other;
a contact portion disposed opposite to a side on which the first fluid container, the second fluid container, the third fluid container, and the fourth fluid container are in contact with the support and disposed adjacent to all the first fluid container, the second fluid container, the third fluid container, and the fourth fluid container;
a detector configured to detect an internal pressure of the first fluid container, an internal pressure of the second fluid container, an internal pressure of the third fluid container, and an internal pressure of the fourth fluid container; and
a computer configured or programmed to obtain information regarding the internal pressure of the first fluid container, the internal pressure of the second fluid container, the internal pressure of the third fluid container, and the internal pressure of the fourth fluid container from the detector and, upon application of an external force to the contact portion from an object, calculate a force acting in a tangential direction on a contact surface between the object and the contact portion; wherein
upon application of the external force to the contact portion from the object, the external force applied to the contact portion from the object is imparted to all the first fluid container, the second fluid container, the third fluid container, and the fourth fluid container through the contact portion; and
when a sum of internal pressures of two fluid containers of the first fluid container, the second fluid container, the third fluid container, and the fourth fluid container is defined as a first internal pressure and a sum of internal pressures of the other two fluid containers of the first fluid container, the second fluid container, the third fluid container, and the fourth fluid container is defined as a second internal pressure, upon application of the external force to the contact portion from the object, the computer calculates the force acting on the contact surface in the tangential direction based on a difference between the first internal pressure and the second internal pressure.

9. The force detector according to claim 8, wherein the contact portion is defined by a fluid bag with a fluid contained therein.

10. The force detector according to claim 9, wherein
each of the first fluid container, the second fluid container, the third fluid container, and the fourth fluid container is defined by a fluid bag with a fluid contained therein; and
the fluid bag defining the first fluid container, the fluid bag defining the second fluid container, the fluid bag defining the third fluid container, the fluid bag defining the fourth fluid container, and the fluid bag defining the contact portion are bonded to each other.

11. The force detector according to claim 10, wherein
the fluid bag defining the first fluid container, the fluid bag defining the second fluid container, the fluid bag defining the third fluid container, the fluid bag defining the fourth fluid container, and the fluid bag defining the contact portion each include a main front surface portion and an outer peripheral portion located on an outer periphery of the main front surface portion; and
part of the outer peripheral portion of the fluid bag defining the contact portion and part of the main front surface portion of the fluid bag defining each of the first fluid container, the second fluid container, the third fluid container, and the fourth fluid container are bonded to each other.

12. The force detector according to claim 10, wherein each of the fluid bag defining the first fluid container, the fluid bag defining the second fluid container, the fluid bag defining the third fluid container, and the fluid bag defining the fourth fluid container has a bag shape defined by outer peripheral portions of two of the sheet-shaped members which are bonded to each other, and each of the fluid bags has a polygonal outer shape while being contracted in plan view.

13. The force detector according to claim 12, wherein each of the fluid bag defining the first fluid container, the fluid bag defining the second fluid container, the fluid bag defining the third fluid container, and the fluid bag defining the fourth fluid container has a rectangular outer shape while being in contracted in plan view.

14. The force detector according to claim 12, wherein a portion at which the outer peripheral portions of the two sheet-shaped members are bonded to each other is provided with a reinforcing portion to increase rigidity.

* * * * *